(12) United States Patent  (10) Patent No.: US 7,909,191 B2
Baker et al.  (45) Date of Patent: Mar. 22, 2011

(54) CONNECTABLE INSTRUMENT TRAYS FOR CREATING A MODULAR CASE

(75) Inventors: Terry L. Baker, Boggstown, IN (US); Rebecca Baker, Boggstown, IN (US)

(73) Assignee: Greatbatch Ltd., Clarence, NY (US)

( * ) Notice: Subject to any disclaimer, the term of this patent is extended or adjusted under 35 U.S.C. 154(b) by 859 days.

(21) Appl. No.: 11/446,613

(22) Filed: Jun. 5, 2006

(65) Prior Publication Data

US 2006/0273084 A1 Dec. 7, 2006

Related U.S. Application Data

(60) Provisional application No. 60/687,510, filed on Jun. 3, 2005.

(51) Int. Cl.
*B65D 21/024* (2006.01)
(52) U.S. Cl. ..................................................... 220/23.4
(58) Field of Classification Search .................. 206/505, 206/503, 600, 386, 577, 223, 216, 506, 510; 220/23.2, 23.89, 23.86, 761, 770, 526, 524, 220/523, 500, 23.6, 630, 634, 625, 628; 292/302, 292/277; D9/760, 759, 756, 737, 443; *B65D 21/028, 21/024, 21/02*
See application file for complete search history.

(56) References Cited

U.S. PATENT DOCUMENTS

| | | | | |
|---|---|---|---|---|
| 144,343 A * | 11/1873 | Martin | ...................... | 220/592.15 |
| 586,122 A * | 7/1897 | Gale | .............................. | 206/510 |
| 1,542,115 A * | 6/1925 | Weis | .............................. | 220/23.2 |
| 1,716,367 A * | 6/1929 | Clayton | ........................ | 220/526 |
| 2,110,921 A * | 3/1938 | Scurlock | ...................... | 220/23.4 |
| 2,540,940 A * | 2/1951 | Ganzer | ........................ | 312/236 |
| 2,876,924 A * | 3/1959 | Chrisman | ........................ | 220/8 |
| 2,944,694 A * | 7/1960 | Kinsey | ............................ | 206/541 |
| 3,589,554 A * | 6/1971 | Smith | ........................ | 220/23.83 |
| 3,635,361 A * | 1/1972 | Hayes | ........................... | 206/510 |
| 3,780,468 A * | 12/1973 | Maffett | ........................ | 43/54.1 |
| 3,939,982 A * | 2/1976 | Russell | ......................... | 206/509 |
| 4,661,326 A * | 4/1987 | Schainholz | ................... | 422/310 |
| 4,799,604 A * | 1/1989 | Okojima et al. | .............. | 220/260 |
| 4,830,200 A * | 5/1989 | Zambano et al. | ........... | 211/133.5 |
| 4,889,254 A * | 12/1989 | Vola | .............................. | 220/23.4 |
| 4,893,719 A * | 1/1990 | Lombardi et al. | ............ | 220/23.4 |
| 4,915,913 A * | 4/1990 | Williams et al. | .............. | 422/119 |
| 5,381,916 A * | 1/1995 | Strawder | ...................... | 220/23.4 |
| 5,424,048 A | 6/1995 | Riley | .............................. | 422/300 |
| 5,441,707 A * | 8/1995 | Lewis et al. | .................... | 422/300 |
| 5,544,969 A * | 8/1996 | Ammon et al. | ............. | 403/322.1 |
| 5,628,970 A * | 5/1997 | Basile et al. | ................... | 422/297 |
| 5,641,065 A * | 6/1997 | Owens et al. | ................... | 206/370 |
| 5,706,968 A * | 1/1998 | Riley | ............................ | 220/326 |
| 5,735,422 A * | 4/1998 | Binter | ......................... | 220/4.21 |
| 5,887,745 A * | 3/1999 | Wood | ............................ | 220/326 |

(Continued)

FOREIGN PATENT DOCUMENTS

JP 08192848 A * 7/1996

*Primary Examiner* — Anthony Stashick
*Assistant Examiner* — Robert J Hicks
(74) *Attorney, Agent, or Firm* — Michael F. Scalise

(57) ABSTRACT

A modular tray and lid combination for use in configuring a containment case includes one or more trays and a single lid. When a plurality of trays are used they are connected together either end-to-end or side-by-side or both. The lid includes a plurality of slide latches that secure the lid to the tray or trays.

20 Claims, 46 Drawing Sheets

U.S. PATENT DOCUMENTS

| | | | |
|---|---|---|---|
| 5,890,613 A * | 4/1999 | Williams | 220/23.4 |
| 6,012,577 A * | 1/2000 | Lewis et al. | 206/370 |
| D421,335 S * | 3/2000 | Linard | D3/314 |
| 6,116,452 A * | 9/2000 | Hamel et al. | 220/318 |
| 6,138,850 A | 10/2000 | Berry, III | 220/4.28 |
| 6,508,495 B1 * | 1/2003 | Riley | 292/152 |
| 6,554,327 B1 * | 4/2003 | Riley | 292/152 |
| 6,592,000 B1 * | 7/2003 | Owens et al. | 220/324 |
| 6,874,634 B2 | 4/2005 | Riley | 206/439 |
| 7,021,485 B1 * | 4/2006 | Baker et al. | 220/326 |
| 2002/0071799 A1 * | 6/2002 | Wood | 422/300 |
| 2002/0079313 A1 * | 6/2002 | Grayson | 220/23.4 |
| 2005/0109775 A1 * | 5/2005 | Meissen | 220/23.6 |
| 2006/0191943 A1 | 8/2006 | Dane et al. | 220/501 |
| 2007/0295721 A1 * | 12/2007 | Van Handel et al. | 220/23.6 |

* cited by examiner

CONNECTABLE INSTRUMENT TRAYS FOR CREATING A MODULAR CASE

CROSS REFERENCES TO RELATED APPLICATIONS

The present application is a regular, continuation-in-part patent application of U.S. Provisional Patent Application Ser. No. 60/687,510, filed Jun. 3, 2005, entitled "Connectable Instrument Trays for Creating a Modular Case" which is hereby incorporated by reference in its entirety. The present application claims the benefit of U.S. Provisional Patent Application Ser. No. 60/687,510.

BACKGROUND OF THE INVENTION

The present invention relates in general to component and/or equipment (containment) cases, including medical instrument cases, that include a modular construction. More specifically, the present invention pertains to the use of connectable modular trays to create the storage or containment portion of a component and/or equipment case. Using connective modular trays permits greater design flexibility and custom sizing of the case. The preferred embodiment of the present invention is described and illustrated in the context of medical instrument cases. As used herein, a containment or medical instrument "case" includes at least one storage or containment tray that is covered and closed by a cooperating lid.

Medical instrument cases are disclosed in the art by various issued patents, wherein the construction of the case is by the use of modular components. For example, U.S. Pat. No. 6,138,850 issued Oct. 31, 2000 to Berry III discloses a modular sterilization container with side pieces, end pieces and corner segments that assemble together enabling a change in the size of the finished case, specifically the tray, by changing the lengths of the side and end pieces. Other structural concepts associated with medical instrument cases that might be broadly classified as "modular" are found in the art in terms of standard-sized holders or standard-sized containers that can be arranged in different locations or patterns within a tray or case. In these instances, the tray size and thus the case size is fixed including its overall shape and construction.

What is missing from the art is a combination of these two concepts. It would be an improvement to the current state of the art to be able to use a modular concept in terms of creating the desired overall size and shape of the case while at the same time providing individual holders, compartments, trays, and/or containers that are sized to accommodate particular sets or groups of components and/or equipment such as medical (or dental) instrumentation. The present invention is directed to providing this unique combination in what is believed to be a novel and unobvious construction.

BRIEF SUMMARY OF THE INVENTION

A modular tray and lid combination for use in configuring a containment case according to one embodiment of the present invention comprises one or more trays and a single lid. When a plurality of trays are used, they are mechanically connected together either end to end or side to side or both. The lid includes a plurality of slide latches that secure the lid to the tray or trays.

One object of the present invention is to provide an improved modular tray and lid combination for a containment case.

Related objects and advantages of the present invention will be apparent from the following description.

DETAILED DESCRIPTION OF THE INVENTION

Figure 1B:
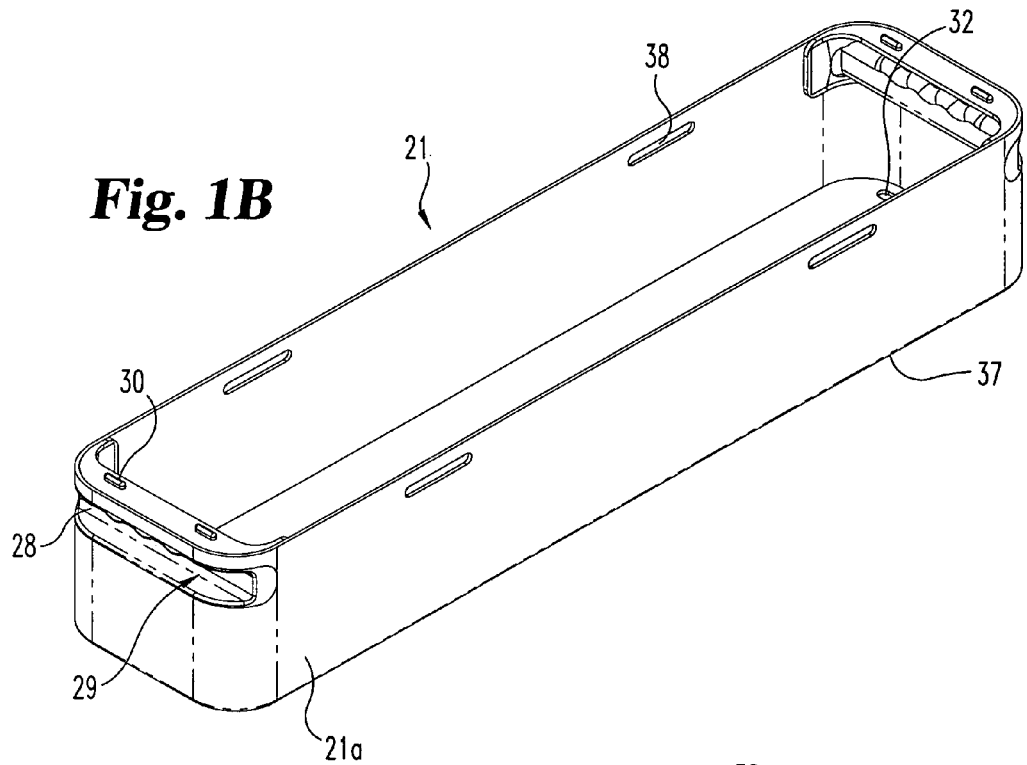
FIG. 1B is a perspective view of a single-wide, double-length tray according to one embodiment of the present invention.

For the purposes of promoting an understanding of the principles of the invention, reference will now be made to the embodiments illustrated in the drawings and specific language will be used to describe the same. It will nevertheless be understood that no limitation of the scope of the invention is thereby intended, such alterations and further modifications in the illustrated device, and such further applications of the principles of the invention as illustrated therein being contemplated as would normally occur to one skilled in the art to which the invention relates.

Figure 1A:
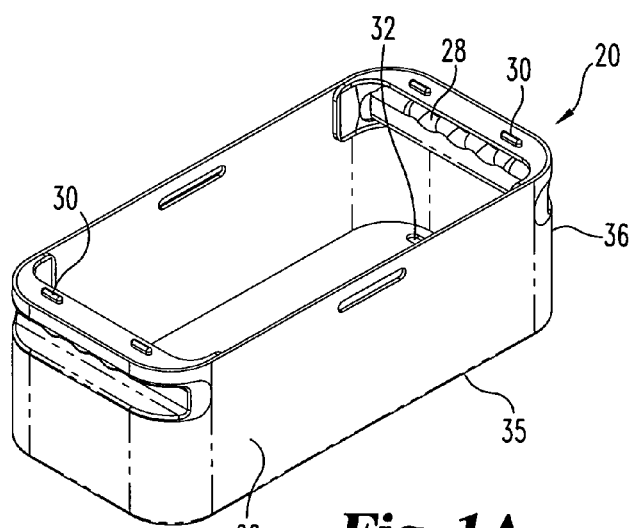
FIG. 1A is a perspective view of a single-wide, single-length tray according to one embodiment of the present invention.
Figure 2B:
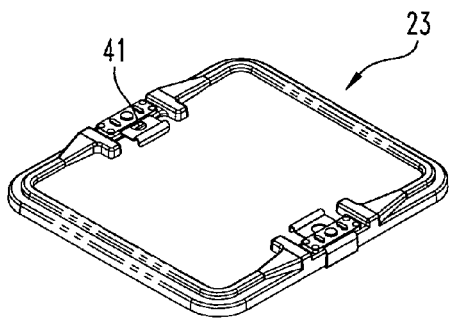
FIG. 2B is a perspective view of a lid constructed and arranged for enclosing a pair of FIG. 1A trays.
Figure 2A:
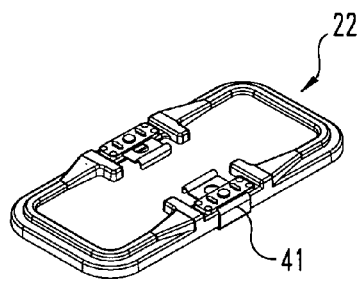
FIG. 2A is a perspective view of a lid that is constructed and arranged for closing the FIG. 1A tray.
Figure 2D:
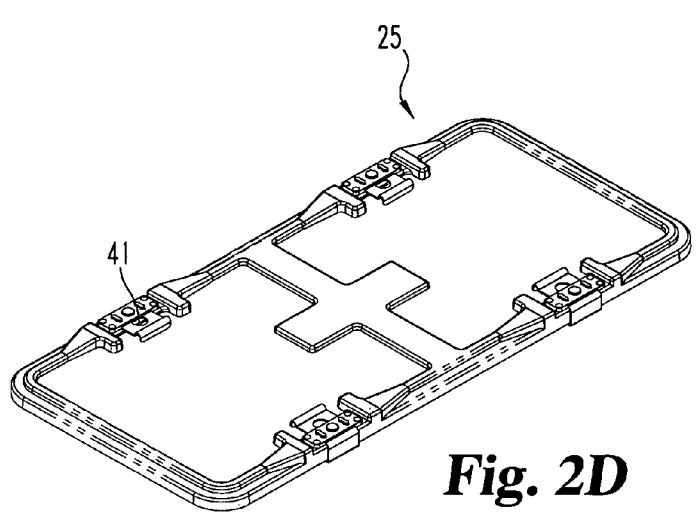
FIG. 2D is a perspective view of a lid constructed and arranged for closing a modular arrangement of trays, either the FIG. 1A tray or the FIG. 1B tray, or a combination resulting in a double wide, double length modular tray combination.
Figure 2C:
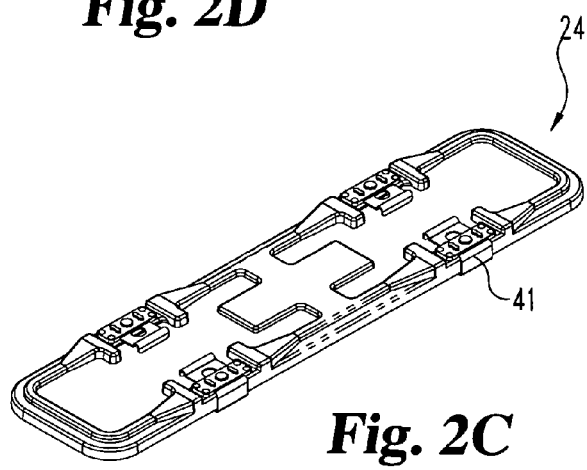
FIG. 2C is a perspective view of a lid constructed and arranged for closing the FIG. 1B tray or a pair of FIG. 1A trays.

Referring to FIGS. 1A, 1B, 2A, 2B, 2C and 2D there is illustrated the basic modular tray and lid components for constructing the containment cases according to the present invention. The preferred embodiments of the present invention are described and illustrated as medical (or dental) instrumentation cases. In FIGS. 1A and 1B the two standard tray sizes include the single-wide, single-length tray 20 and the single-wide, double-length tray 21. Each modular tray, as disclosed herein, includes a pair of side walls and a pair of end walls that define an interior and an upper opening. The width of tray 20 is the same as the width of tray 21. Two trays 20 assembled (connected) end to end are equal in length to tray 21. In terms of the present invention, only single-wide trays are contemplated. Preferably, tray 20 has a 2:1 length to width aspect ratio for maximum versatility and this aspect ratio, or multiples thereof, is continued for all disclosed trays and lids. While a 2:1 aspect ratio is described, other dimensional variations and aspect ratios are contemplated and equally acceptable.

Since all trays are constructed and arranged with a structural configuration that allows the trays to be connected to one another, a double-wide tray is created by fitting together or otherwise connecting together two single-wide trays, side by side. One preferred embodiment for connecting together a plurality of trays in terms of rigidity and strength is to use a support plate that is sized and shaped similar to the selected lid for the particular selection and arrangement of modular trays (see FIGS. 19A-19C). One option for connecting or attaching each support plate to its corresponding arrangement of modular trays is to provide tapped or threaded holes in the bottom surface of each tray and a corresponding clearance hole (countersunk) in the selected support plate. Considering that the thickness of the metal for each modular tray may not support tapped or threaded holes, preferably clearance holes would be provided and used for the installation of a threaded fastener, nut, or insert. The use of flathead screws completes the connection and maintains a smooth, flat surface for the bottom surface of each support plate and thus for each constructed containment case, see FIGS. 20 and 21 for example.

Another style of connecting feature or structure that is suitable for the assembly or connection of one tray to another tray is preferably the use of a male form or forms on one tray and a cooperating female form or forms on the other (connecting) tray. Depending on the design specifics, this approach enables a snap-together style of assembly or connection for the selected modular trays, see FIGS. 36-44. By providing substantially flat and smooth side panels and end panels for each of the modular trays, the options for the referenced connecting feature can also include headed pins, rivets, and clips, as well as similar mechanical components and fasteners that would insert into aligned holes, slots, or notches, respectively, see FIGS. 45-51. In the case of an insertable headed pin or rivet, aligned holes in abutting side walls and/or abutting end walls of the modular trays are used. As one example, with a hollow pin and an inserting post, one portion is inserted through the aligned clearance holes and the other portion is then configured to press into the hollow interior. A rivet or pop rivet performs much the same function in the same manner, except that a rivet or pop rivet would be considered more of a permanent connection, while the push pin and inserted post can be manually disassembled.

With reference to FIGS. 2A-2D, the four standard lids 22, 23, 24 and 25 are illustrated. Lid 22 corresponds to and is used on the single-wide, single-length tray 20. If two trays 20 are assembled side by side, then lid 23 is used. Lid 24 corresponds to and is used on the single-wide, double-length tray 21. Lid 24 is also used when two trays 20 are assembled end to end. Lid 25 is used when two trays 21 are assembled side by side or when one tray 21 is assembled to two trays 20. A third variant for lid 25 is when four trays 20 are assembled together in a two by two pattern. Each of these tray and lid combinations are illustrated in FIGS. 3 through 16. For each lid style or variation disclosed herein, there is a corresponding or matching support plate with generally the same length to width aspect ratio as the lid, see FIGS. 21-35.

Figure 3:
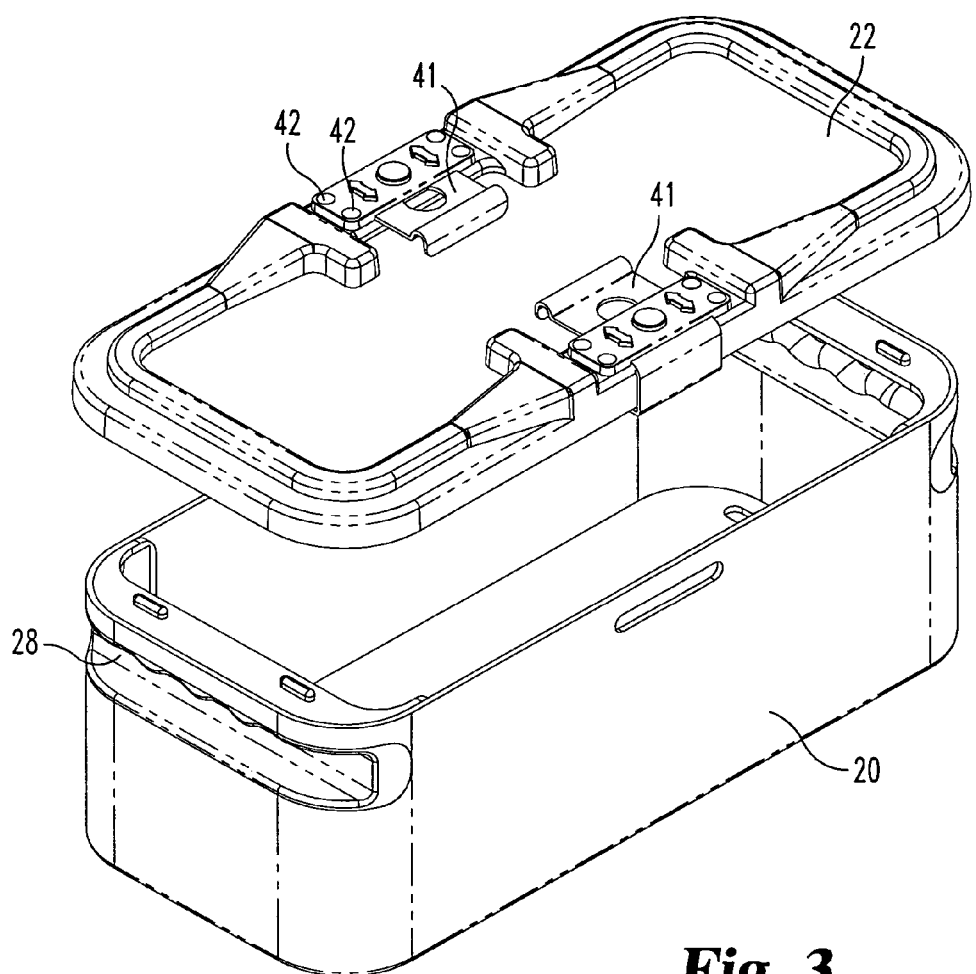
FIG. 3 is an exploded view of the FIG. 1A tray and FIG. 2A lid.

Referring now to FIG. 3, an exploded view of the FIG. 1A tray 20 in combination with the FIG. 1B lid 22 is illustrated. As can be seen from this drawing, the tray 20 includes a molded plastic handle 28 (see FIG. 17) at each end that securely assembles into the corresponding opening in the metal end wall of tray 20. A recessed channel 29 defined by each handle 28 is used for lifting of the tray and/or the assembled case. The "corners" of each tray 20 (and 21) are curved and an end portion of each handle 28 extends into the curvature of its adjacent "corner". The upper surface of each handle includes a pair of spaced-apart raised oblong buttons 30. The bottom panel 20a of tray 20 and the bottom panel 21a of tray 21 each define a corresponding pair of spaced-apart oblong openings 32 corresponding to each handle in terms of location and spacing. Accordingly, when trays are stacked, without lids, an interfit is achieved by the handle buttons 30 of the lower tray fitting into the openings 32 of the upper tray.

The length dimension side wall 35 of each tray 20 defines a centered, oblong slide latch slot 36. Due to the 2:1 length ratio between trays 21 and 20, the length dimension side wall 37 of each tray 21 defines a pair of spaced-apart, oblong slide latch slots 38. The spacing of slots 38 corresponds to the spacing of slots 36 when two trays 20 are assembled (connected) end to end. The handles of tray 21 are the same as handles 28, including the channel 29 and the pair of raised oblong buttons 30. As such, two trays 20 assembled end to end can be stacked with one tray 21 (all without lids) either on top or on the bottom. The buttons 30 and openings 32 will be in alignment due to the 2:1 length ratio between tray 21 and tray 20. All other dimensions and spacings are set so that the two trays 20, assembled end to end, are virtually identical in form, fit and function to one tray 21, except two separate tray compartments are provided.

Figure 4:
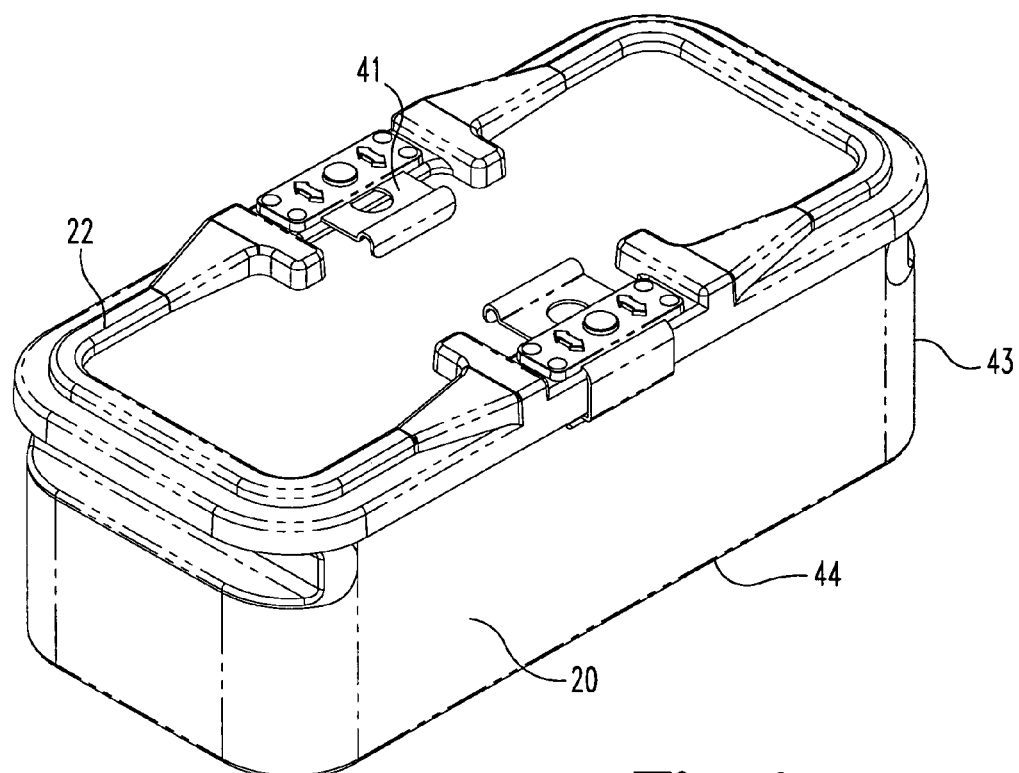
FIG. 4 is a perspective view of the FIG. 3 combination in a closed condition.

Referring to FIG. 4, tray 20 and lid 22 are illustrated in their assembled (closed) condition with the lid 22 securely attached to tray 20 by the use of two slide latches 41. Each slide latch is attached to lid 22, preferably by the use of four rivets 42. These same rivets also secure together several component parts that comprise slide latch 41.

Each slide latch 41 includes a movable slide portion 43 with an inwardly directed lip 44. This lip 44 is constructed and arranged to fit into the corresponding slot 36 or 38 in the tray side wall, either 35 or 37, respectively. With the slide latch 41 riveted to the lid and with lip 44 inserted into the corresponding slot, the lid is secured to the tray so as to close off the upper edge opening of the tray. The pair of slide latches 41 on each side of lids 24 and 25 are positioned so as to correspond to the slot locations in tray 21 and to the slot locations in two trays 20 once assembled end to end.

It will be understood that with the lid attached to a tray, the handle buttons are covered and thus not accessible as a means for stacking. However, the raised portions and resulting relief or recessed portions of each lid 22-25 are constructed and arranged to be stacking compatible with the size and shape of the outer or bottom surface of the bottom panel 20a, 21a of each tray 20, 21, respectively. In this way, whether or not the lids are attached, the trays and cases are fully stackable one on top of the other, regardless of the modular combination of trays that is selected for creating a particular style of instrumentation case. The attention given to the 2:1 sizing and the duplication of features means that two single-length trays 20 are equivalent to one double-length tray 21 whether as a single-width unit or as a double-width unit.

Figure 5:
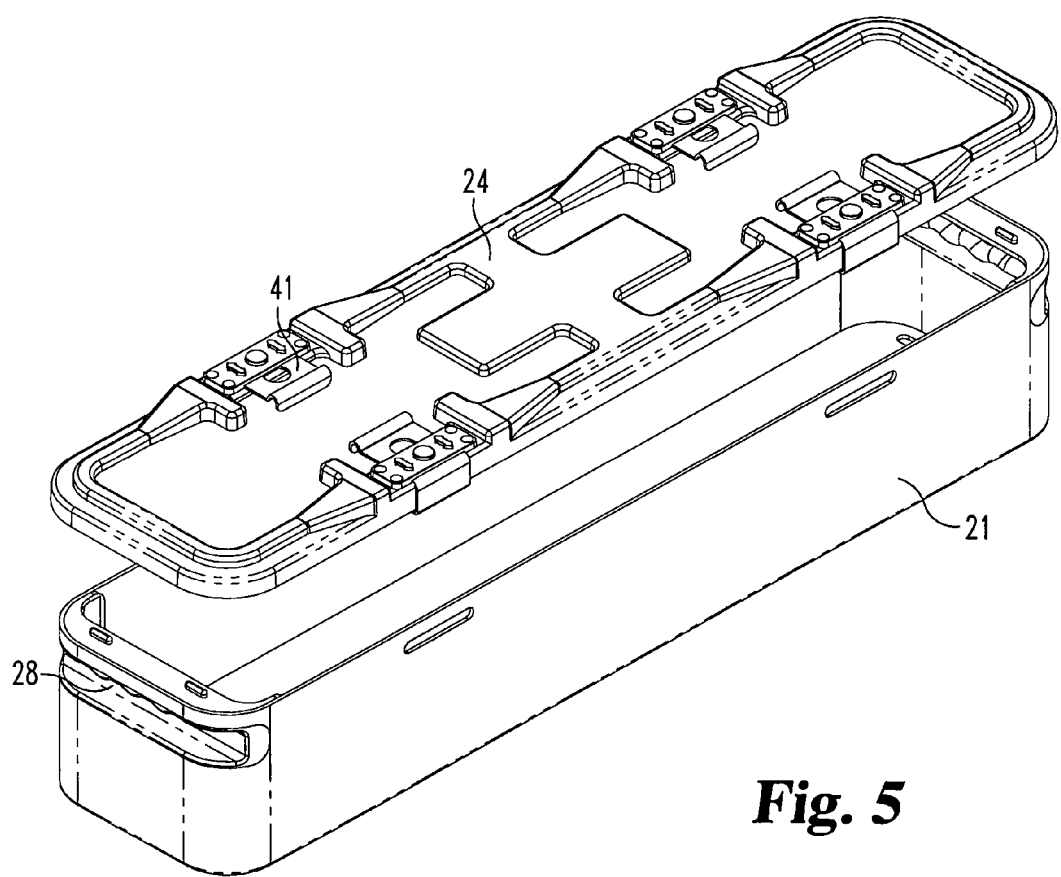
FIG. 5 is an exploded view of the FIG. 1B tray and FIG. 2C lid according to the present invention.
Figure 6:
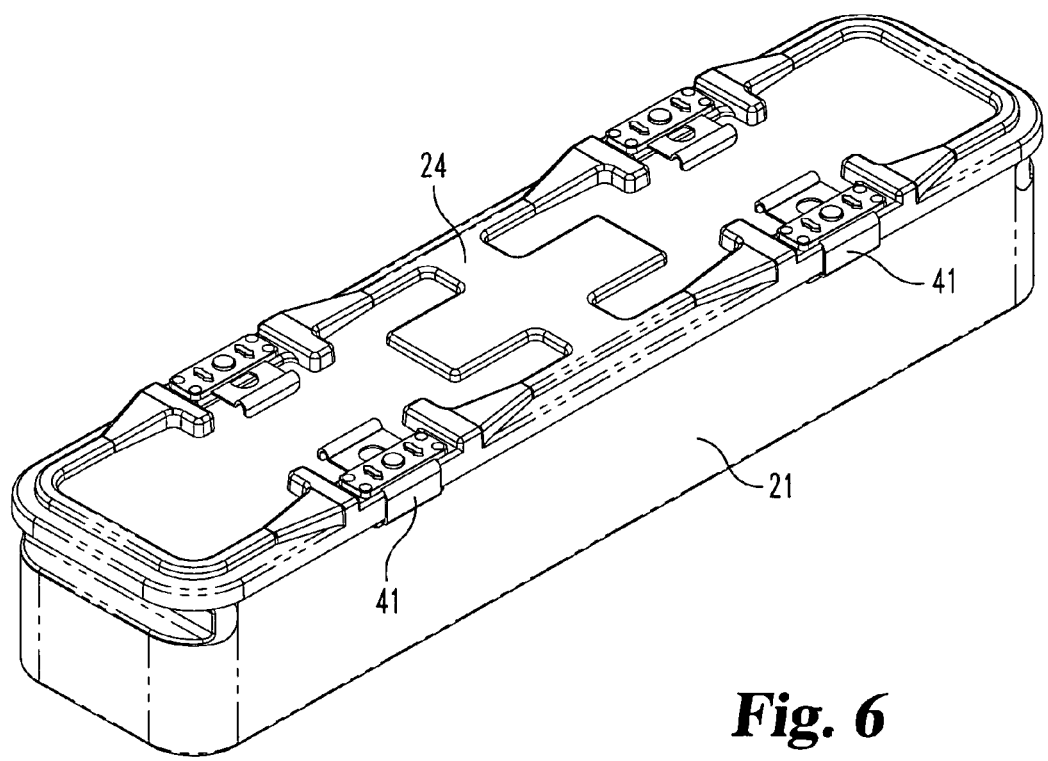
FIG. 6 is a perspective view of the FIG. 5 combination in a closed condition.
Figure 7:
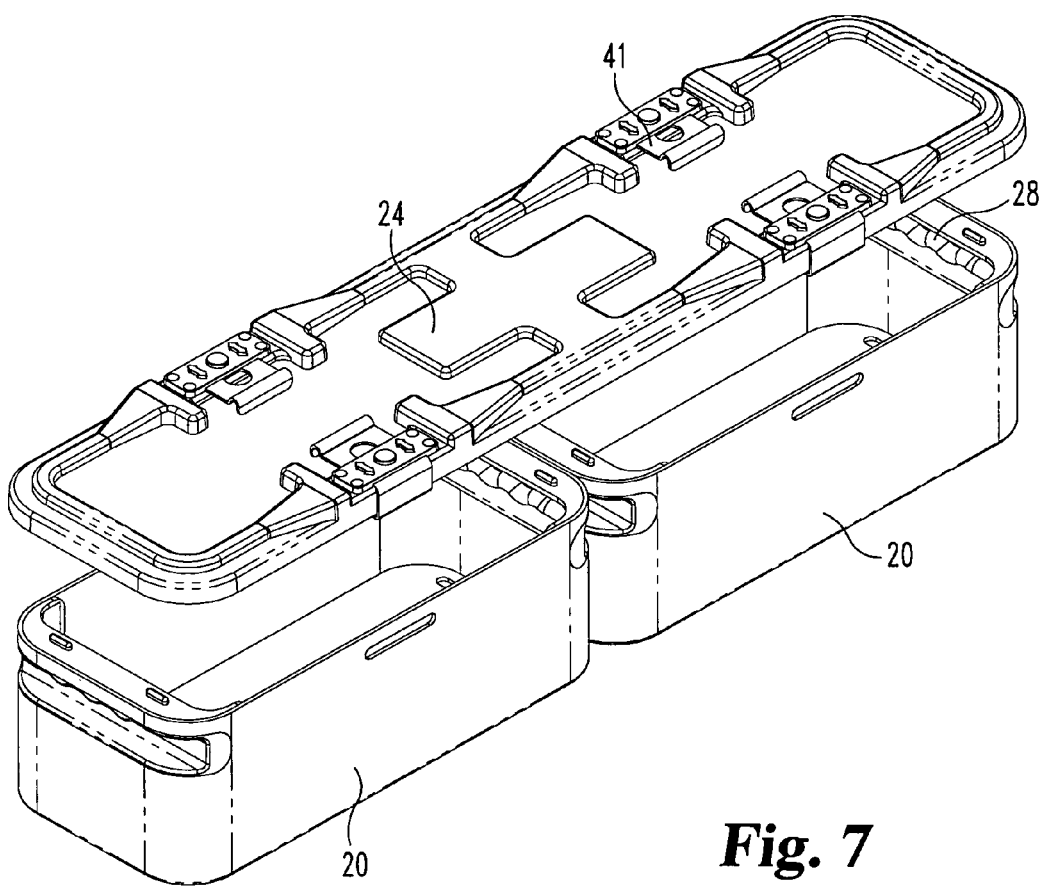
FIG. 7 is an exploded view of a pair of FIG. 1A trays and the FIG. 2C lid according to the present invention.
Figure 8:
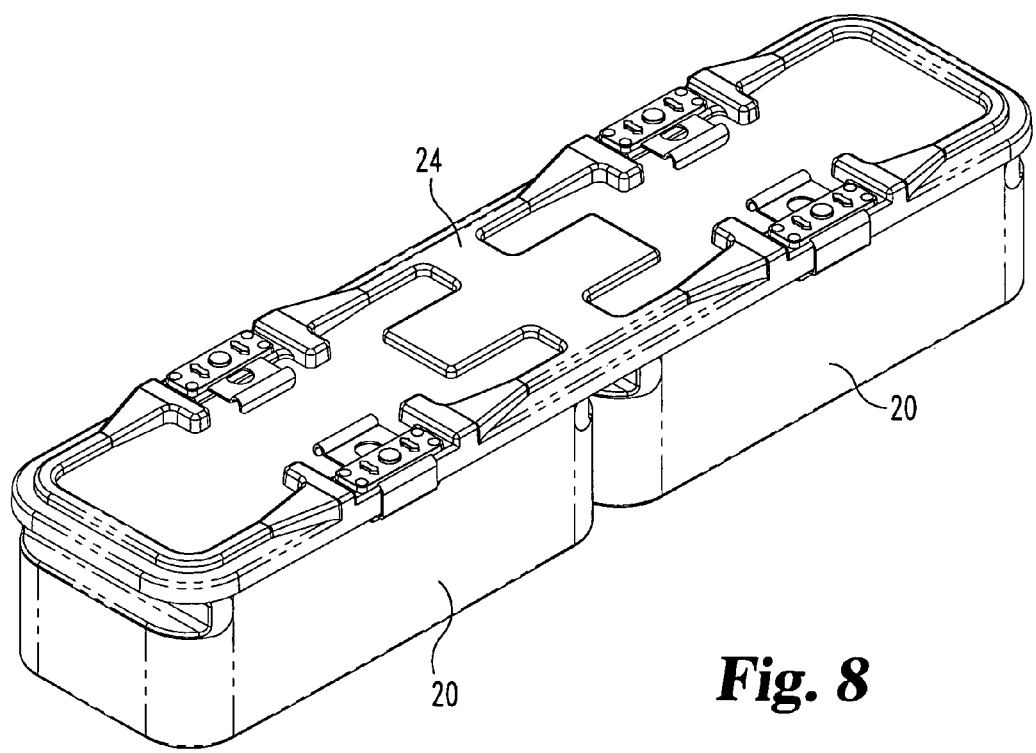
FIG. 8 is a perspective view of the FIG. 7 combination in a closed condition.
Figure 19A:
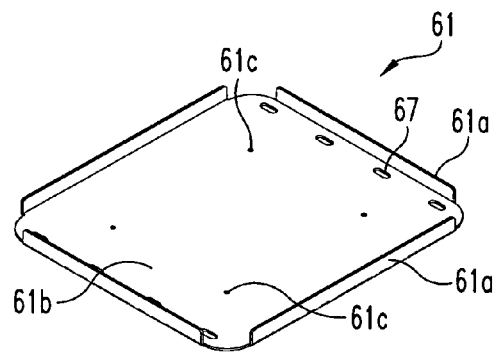
FIGS. 19A, 19B, 19C are perspective views of a support plate suitable to be attached to a plurality of modular trays according to the present invention.
Figure 19B:
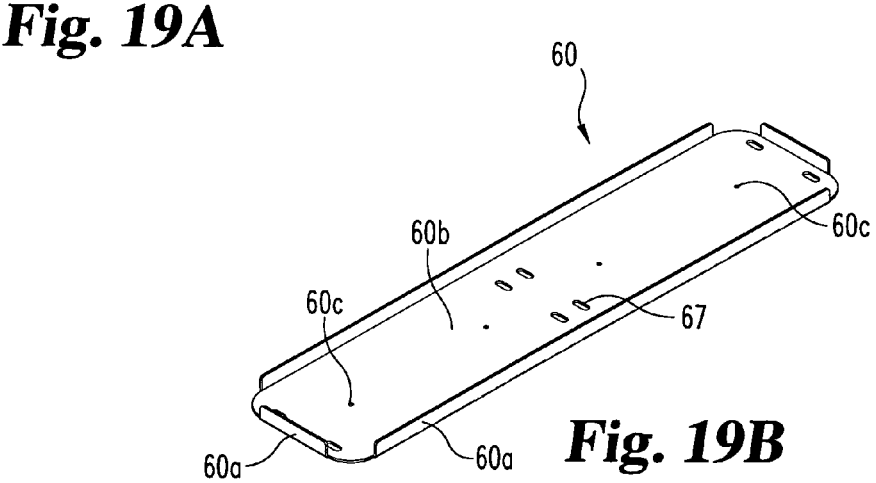

Referring now to FIGS. 5 and 6, the open and closed conditions for tray 21 and lid 24 are illustrated. The slide latches 41 are the same as those used on the single length tray 20 and all other characteristics and features are the same, except for the double length. However, lid 24 is the same lid that is used when two trays 20 are assembled end to end, see FIGS. 7 and 8. The corresponding support plate 60 for the arrangement of FIGS. 7 and 8 is illustrated in FIG. 19B and further illustrated in FIGS. 21-23.

Figure 9:
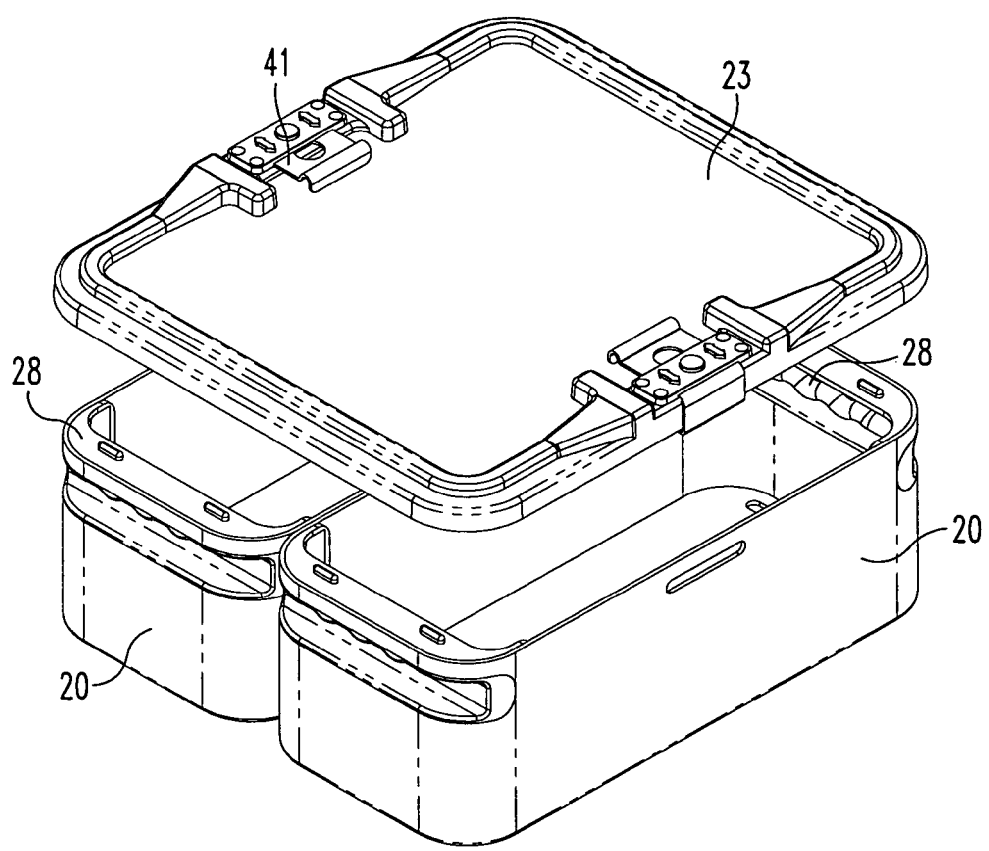
FIG. 9 is an exploded view of two FIG. 1A trays and the FIG. 2B lid according to the present invention.
Figure 10:
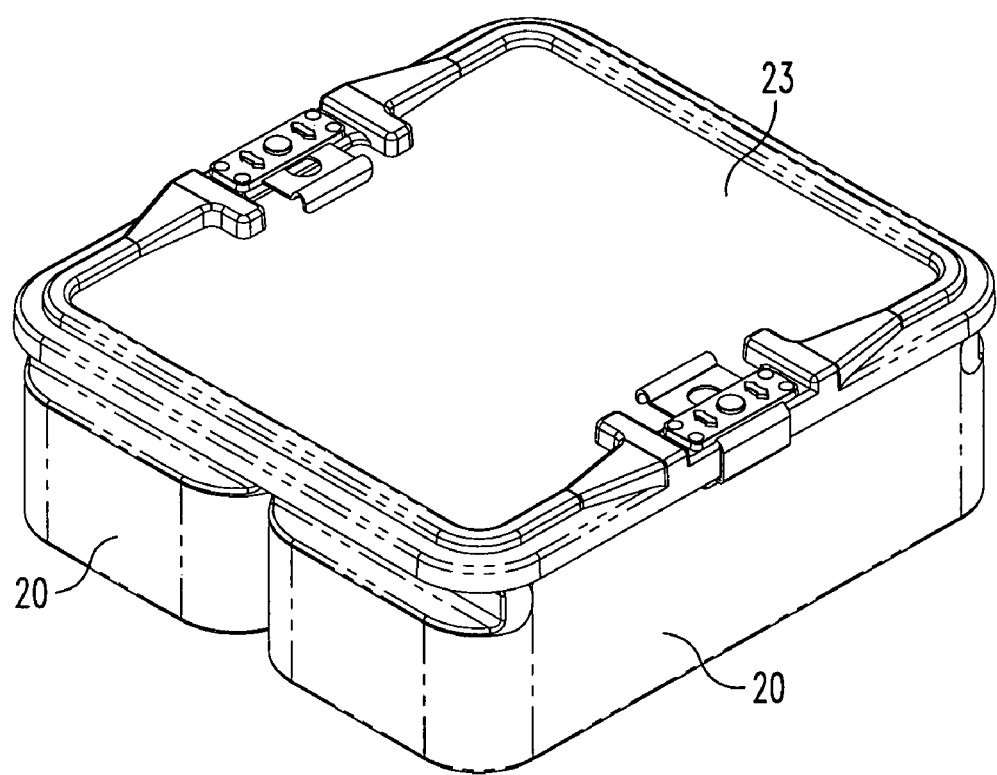
FIG. 10 is a perspective view of the FIG. 9 combination in a closed condition.

Referring now to FIGS. 9 and 10, the combination of lid 23 and two side by side trays 20 is illustrated. FIG. 9 represents the open condition while FIG. 10 represents the closed or latched condition. Slide latches 41 are assembled to lid 23 as previously described in terms of the other tray embodiments and modular arrangements. The corresponding support plate 61 for the arrangement of FIGS. 9 and 10 is illustrated in FIG. 19A and further illustrated in FIGS. 24-26.

Figure 11:
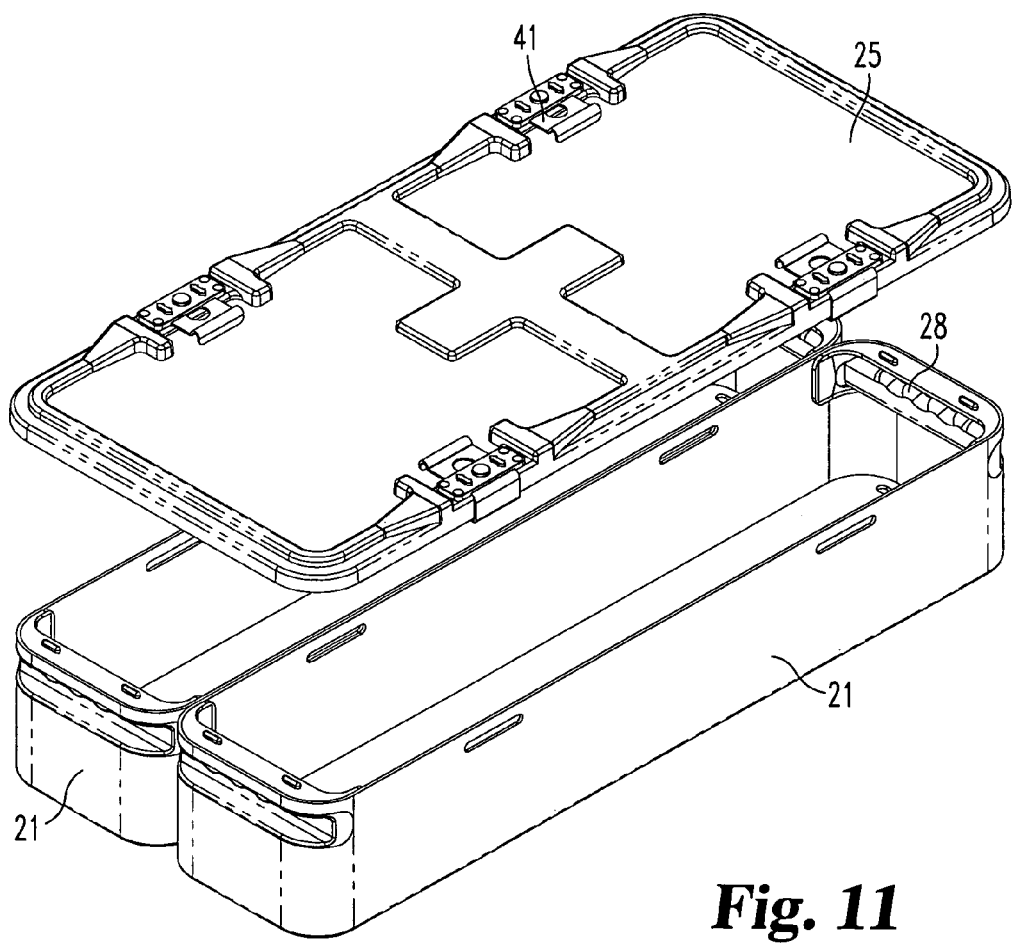
FIG. 11 is a perspective view of two FIG. 1B trays and the FIG. 2D lid.
Figure 12:
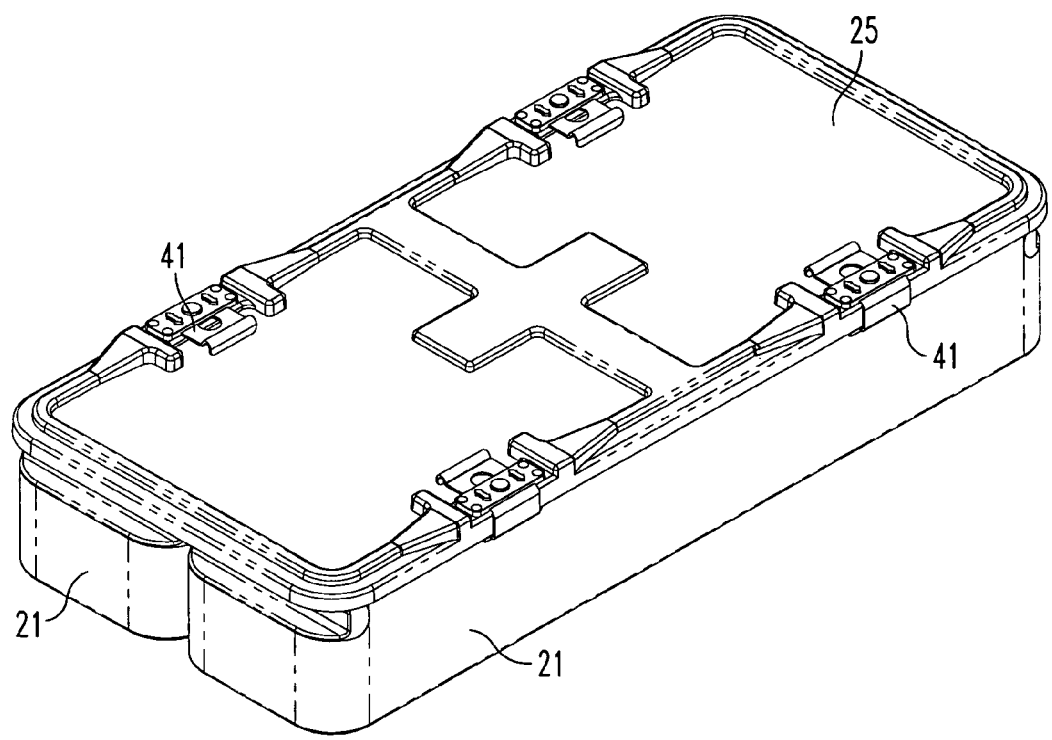
FIG. 12 is a perspective view of the FIG. 11 combination in a closed condition.
Figure 19C:
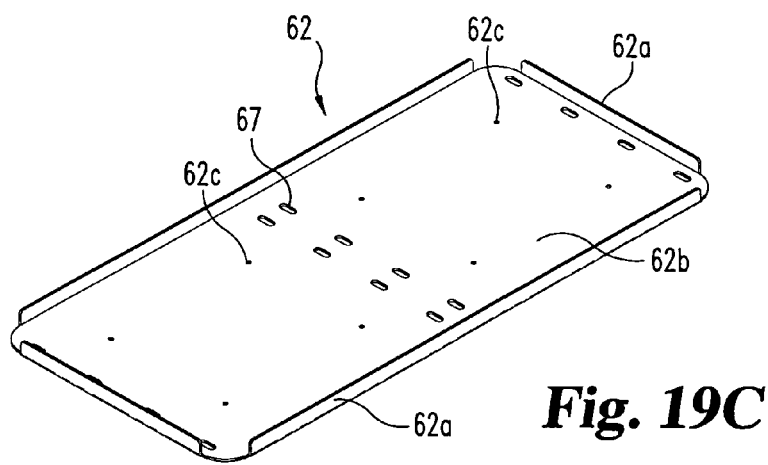

Referring now the FIGS. 11 and 12 the combination of lid 25 and two side by side trays 21 is illustrated. FIG. 11 represents the open condition while FIG. 12 represents the closed or latched position. Slide latches 41 are assembled to lid 25 as previously described in terms of the other tray embodiments and modular arrangements. The corresponding support plate 62 for the arrangement of FIGS. 11 and 12 is illustrated in FIG. 19C and further illustrated in FIGS. 27-29.

Figure 13:
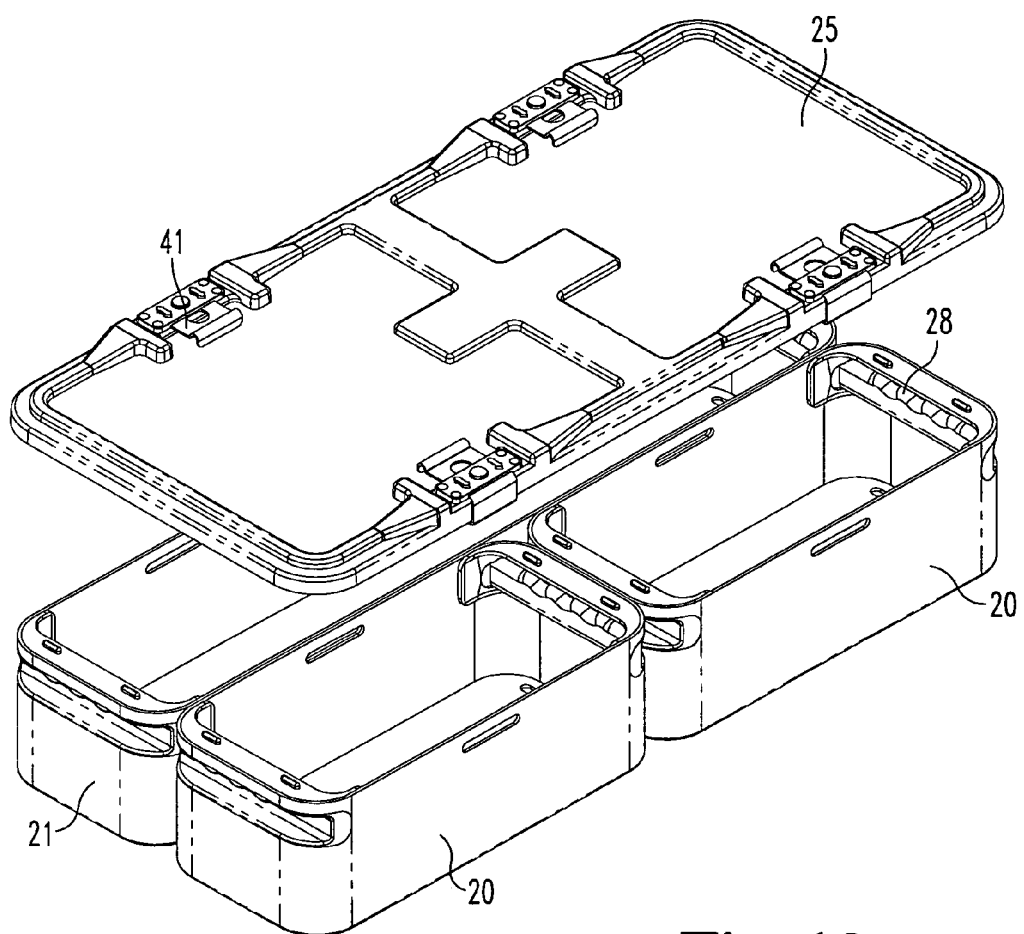
FIG. 13 is an exploded view of two FIG. 1A trays in combination with one FIG. 1B tray and the FIG. 2D lid according to the present invention.
Figure 14:
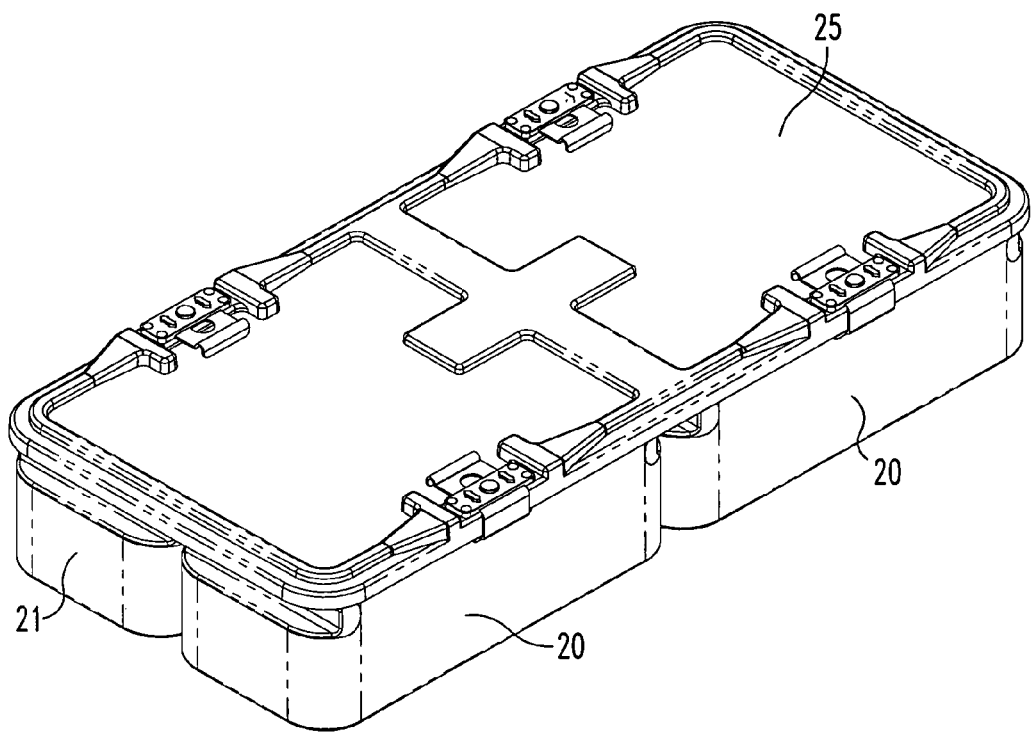
FIG. 14 is a perspective view of the FIG. 13 combination.

Referring now the FIGS. 13 and 14 the combination of lid 25 and one tray 21 side by side with two end to end trays 20 is illustrated. FIG. 13 represents the open condition while FIG. 14 represents the closed or latch condition. Slide latches 41 are assembled to lid 25 as previously described in terms of the other tray embodiments and modular arrangements. The corresponding support plate 62 for the arrangement of FIGS. 13 and 14 is illustrated in FIG. 19C and further illustrated in FIGS. 30-32.

Figure 15:
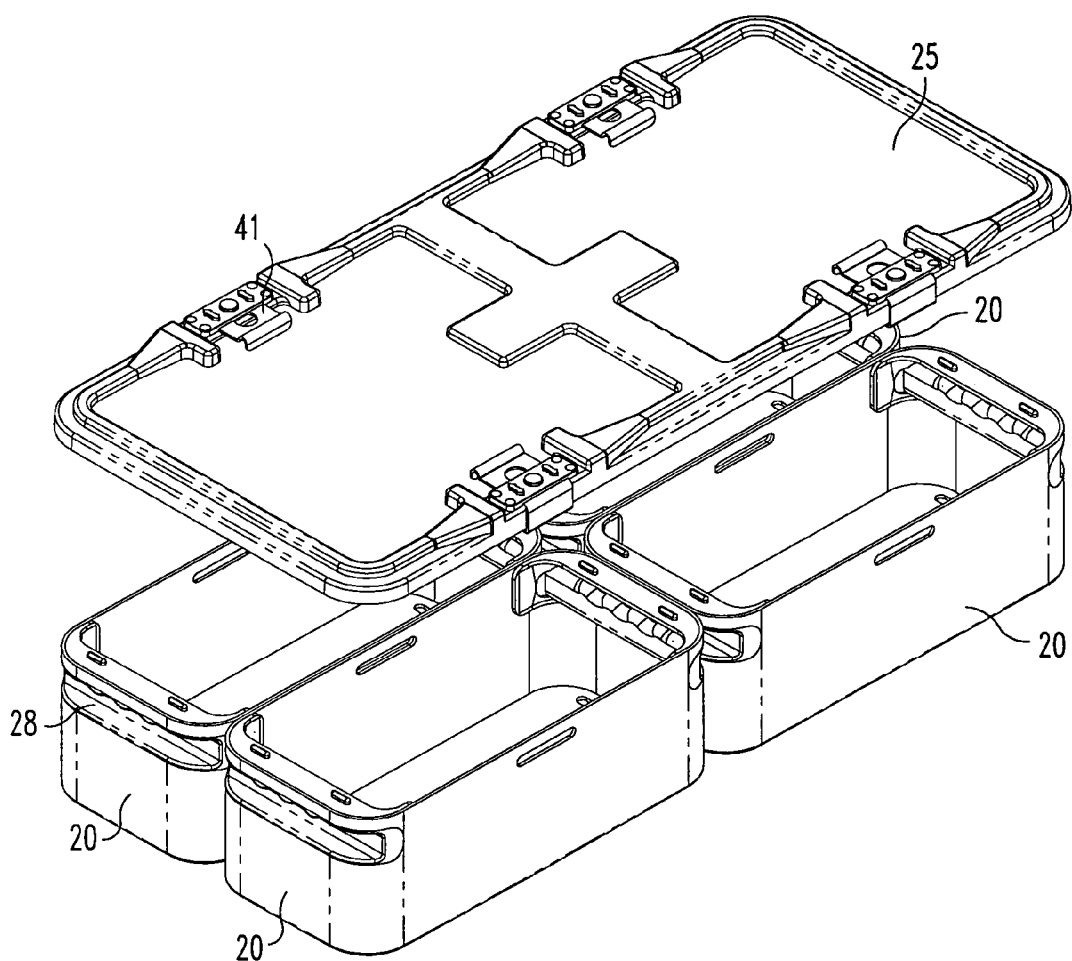
FIG. 15 is an exploded view of four FIG. 1A trays and the FIG. 2D lid according to the present invention.
Figure 16:
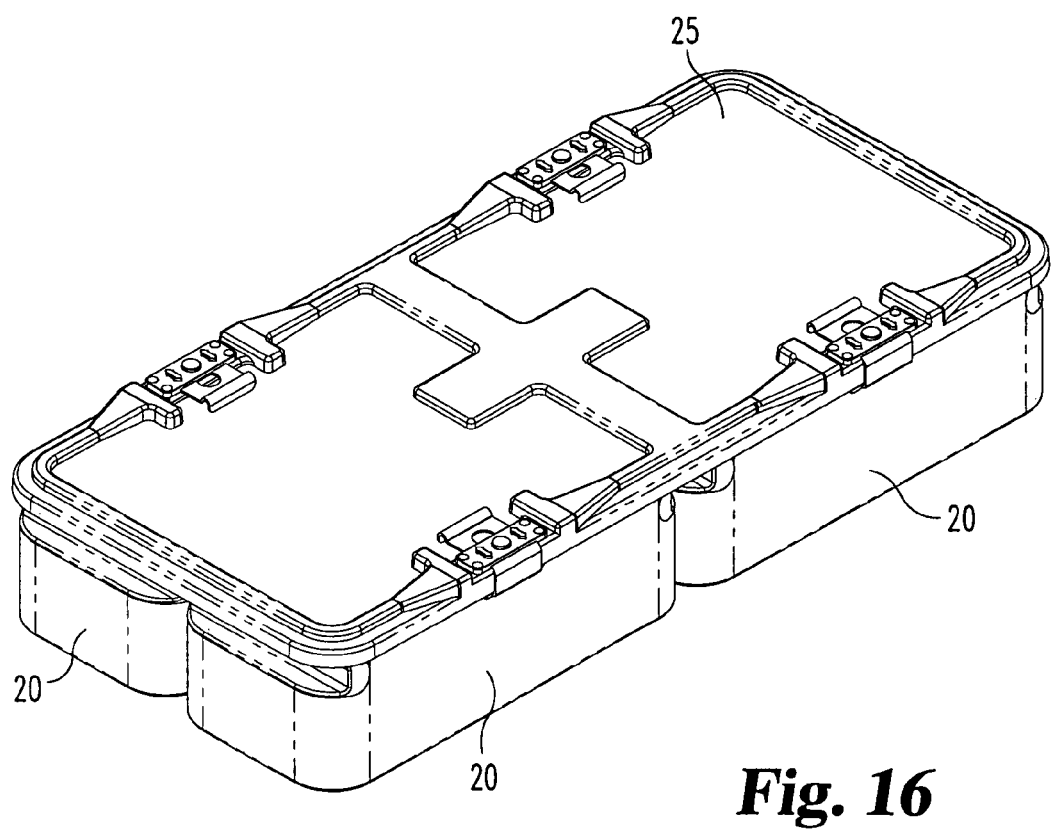
FIG. 16 is a perspective view of the FIG. 15 combination in a closed condition.

Referring now to FIGS. 15 and 16 the combination of lid 25 and four trays 20 arranged side by side and end to end is illustrated. FIG. 15 represents the open condition while FIG. 16 represents the closed or latched condition. Slide latches 41 are assembled to lid 25 as previously described in terms of the other tray embodiments and modular arrangements. The corresponding support plate 62 for the arrangement of FIGS. 15 and 16 is illustrated in FIG. 19C and further illustrated in FIGS. 33-35.

Figure 17:
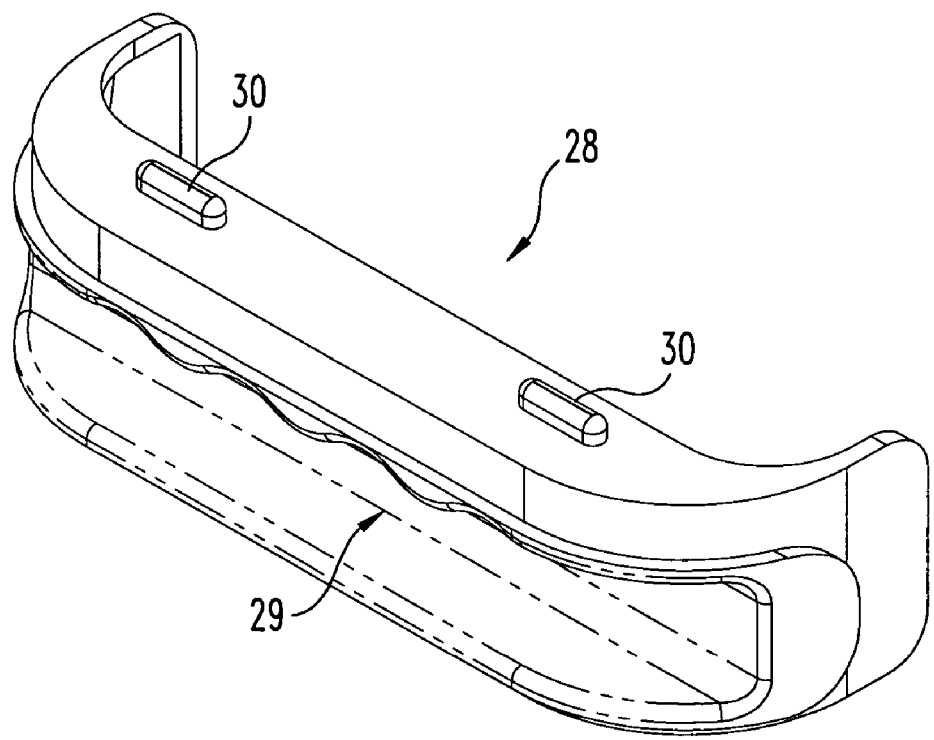
FIG. 17 is a perspective view of a tray handle comprising a portion of the FIG. 1A and FIG. 1B trays.

Referring now to FIG. 17 the details of handle 28, as previously described, are illustrated. This enlarged illustration provides a clearer picture of channel 29 and the raised stacking buttons 30.

Figure 18:
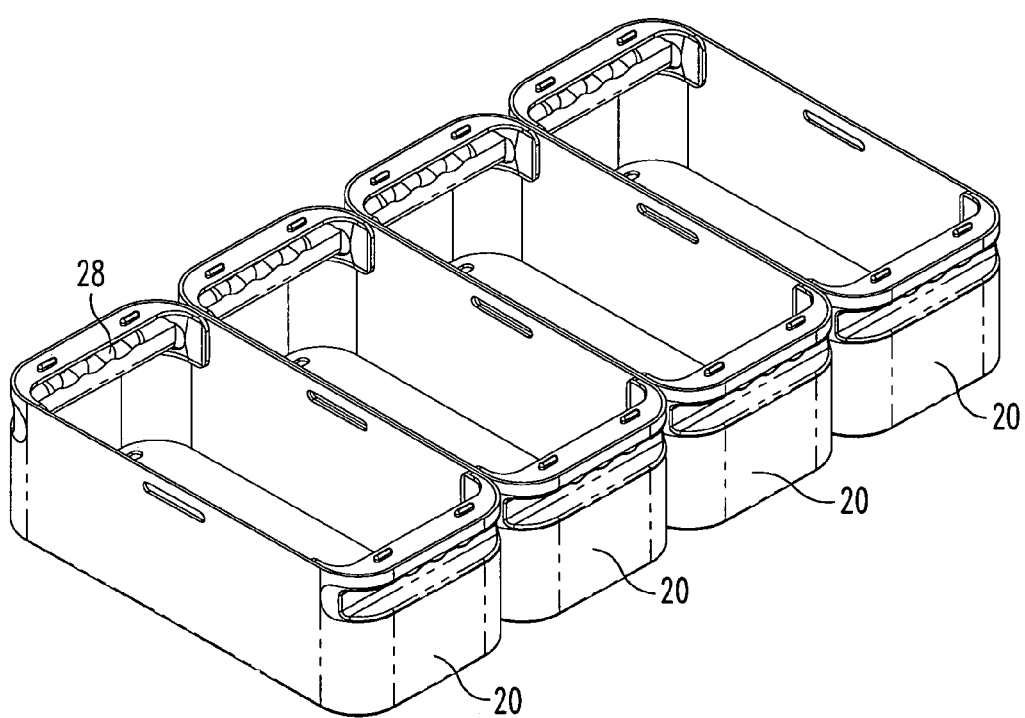
FIG. 18 is a perspective view of four FIG. 1A trays assembled side by side according to another embodiment of the present invention.

Referring now to FIG. 18, another embodiment of the present invention is illustrated. Due to the ability to connect together trays 20, trays 21 and a combination of trays 20 and 21, it is possible to provide other modular configurations, such as the side by side assembly of four trays. If tray 20 does not have a 2:1 length to width aspect ratio, the length of the FIG. 18 configuration will not correspond to either two trays 20 assembled end to end or one tray 21. This means that lid 25 is not compatible in terms of size and shape. If a lid is desired to create a case, then a new, "non-standard" lid would be required. The point of the FIG. 18 illustration is to illustrate that virtually any modular configuration of trays 20 and 21 is possible, regardless of the length to width aspect ratio, due to the fact that each side wall and each end of each tray includes a connection feature or structure for connection of the various trays in a side by side or end to end relationship. If tray 20 is constructed and arranged with a 2:1 length to width aspect ratio, then the FIG. 18 configuration would have a peripheral size and shape equal to the configurations of FIGS. 11 through 16. Then lid 25 would be compatible with the four tray configuration of FIG. 18.

The present invention has been described as including a means, feature or structure to enable one tray to connect to another tray—whether end to end or side by side and whether utilizing tray 20 to tray 20, tray 21 to tray 21, or some combination of trays 20 to tray 21. With regard to the specifics of the interconnection technique, the preferred configuration for the present invention is to incorporate a support plate similar in style and function to support plates 60, 61, and 62. Another connection or assembly option contemplated as part of the present invention is to use a snap-fit scheme. With a snap-fit scheme, the various trays can be manually manipulated into various modular configurations to create the desired case and just as easily disconnected to change to a different configuration for another style of case. Other techniques that are considered for this interconnection technique include using various clips and pins, or perhaps a combination of keys and keyways or quarter turn fasteners.

With reference to FIGS. 19A-19C, the details of each support plate will be described. Each support plate 60, 61, and 62 includes a raised edge lip 60a, 61a, and 62a, respectively, along a portion of each length side and along a portion of each width side. Each substantially flat main body panel 60b, 61b, and 62b, respectively, defines at least one clearance hole 60c, 61c, and 62c, respectively, countersunk from the opposite (bottom) side. In order to accept a threaded fastener or similar mechanical fastener for anchoring each support plate 60, 61, and 62 to its corresponding arrangement of two or more modular trays, threaded inserts (not illustrated) can be installed into the corresponding trays, or if the bottom panel thickness of the tray is sufficient, the receiving holes can be internally threaded.

Figure 20:
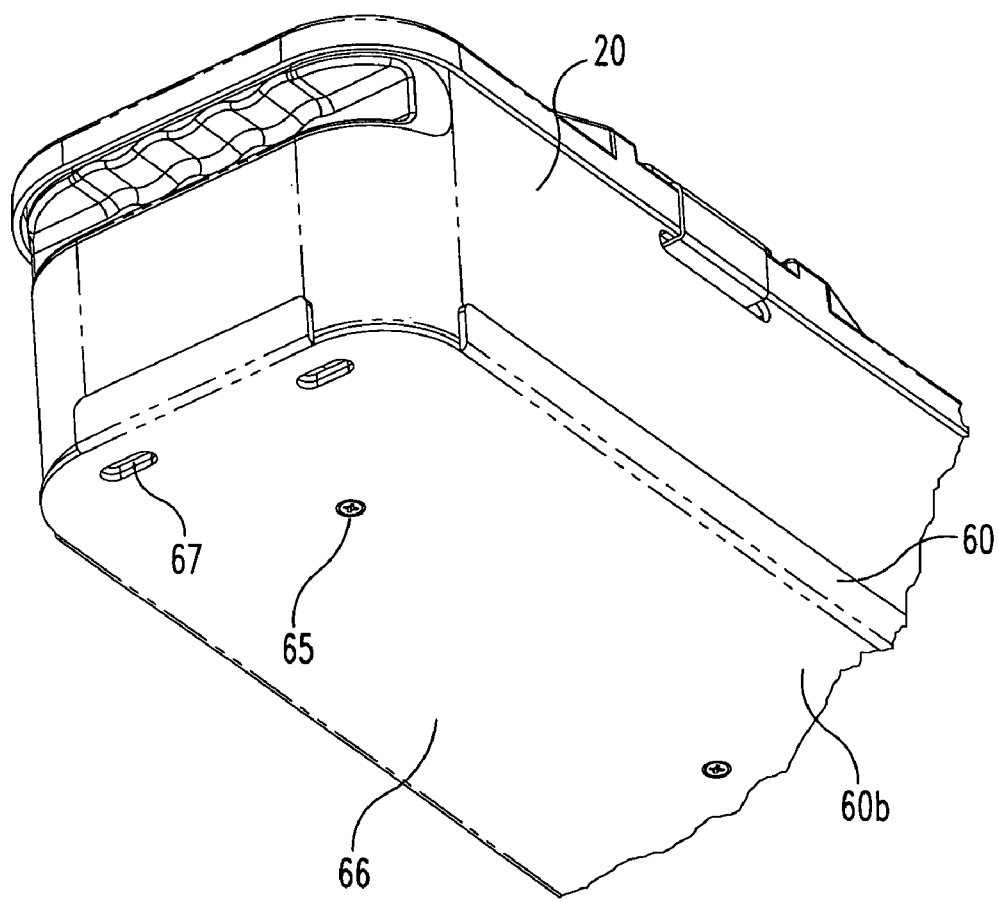
FIG. 20 is a partial, bottom perspective view of one support plate (FIGS. 19A-19C) as attached to a modular tray, according to the present invention.

The raised edge lips 60a, 61a, and 62a fit around the side walls and end walls of the modular trays, as illustrated in FIG. 20 and the support plates are connected to the trays by the fasteners. This arrangement guarantees that the grouping of modular trays will be securely and rigidly held together in the selected side-by-side or end-by-end, or both, pattern and movable as a unit in the form of an assembled containment case. The use of flathead screws 65 allows the bottom surface 66 of the main body panel 60b to remain smooth and flat. With continued reference to FIG. 20, the oblong slot 67, defined by panel 60b (and by panels 61b and 62b), are sized, spaced, and arranged for receiving the raised, oblong buttons 30 of the cooperating handles 28 of the modular trays that are beneath the referenced tray in a stacked arrangement. Oblong slots 67 are aligned with oblong openings 32 in the bottom panels 20a and 21a of the two "standard" modular trays 20 and 21, respectively. This allows the oblong buttons to actually extend through both the support plate main body panel and the tray bottom panel.

Figure 21:
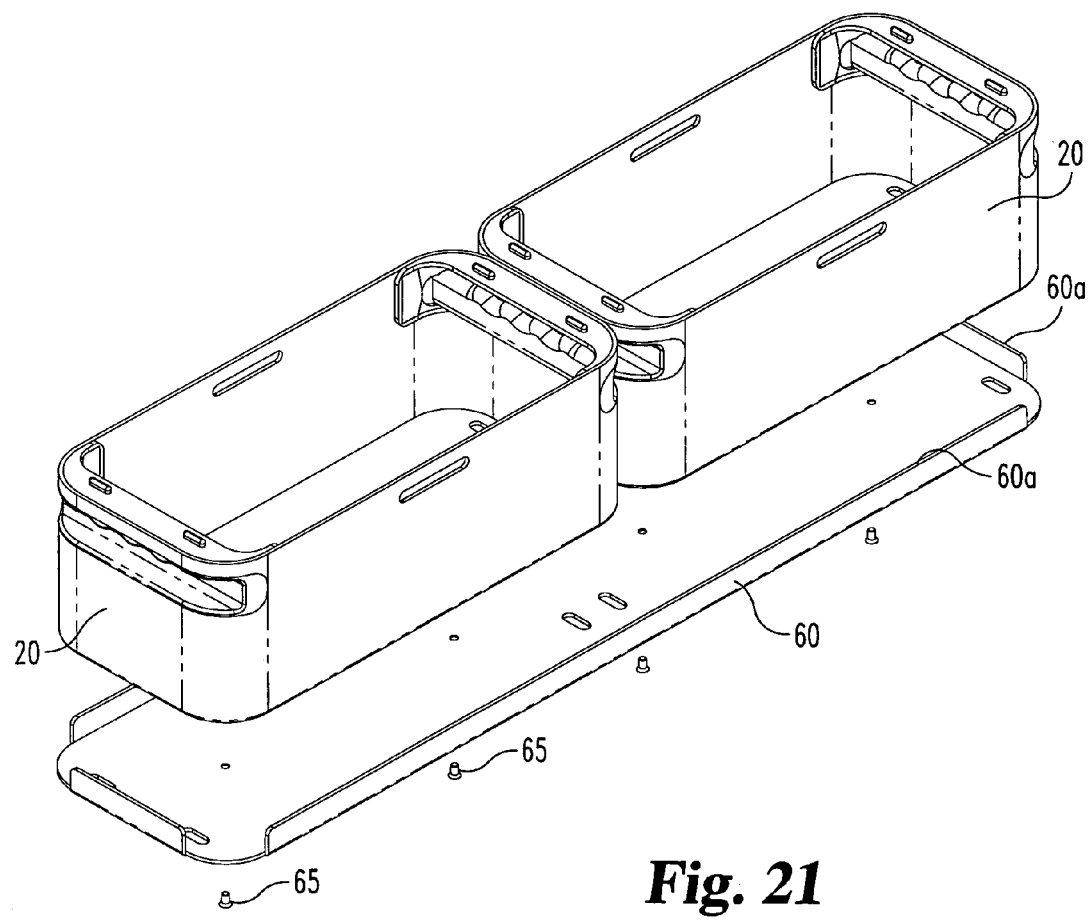
FIG. 21 is an exploded view of a support plate and two modular trays arranged for assembly by mechanical fasteners.
Figure 22:
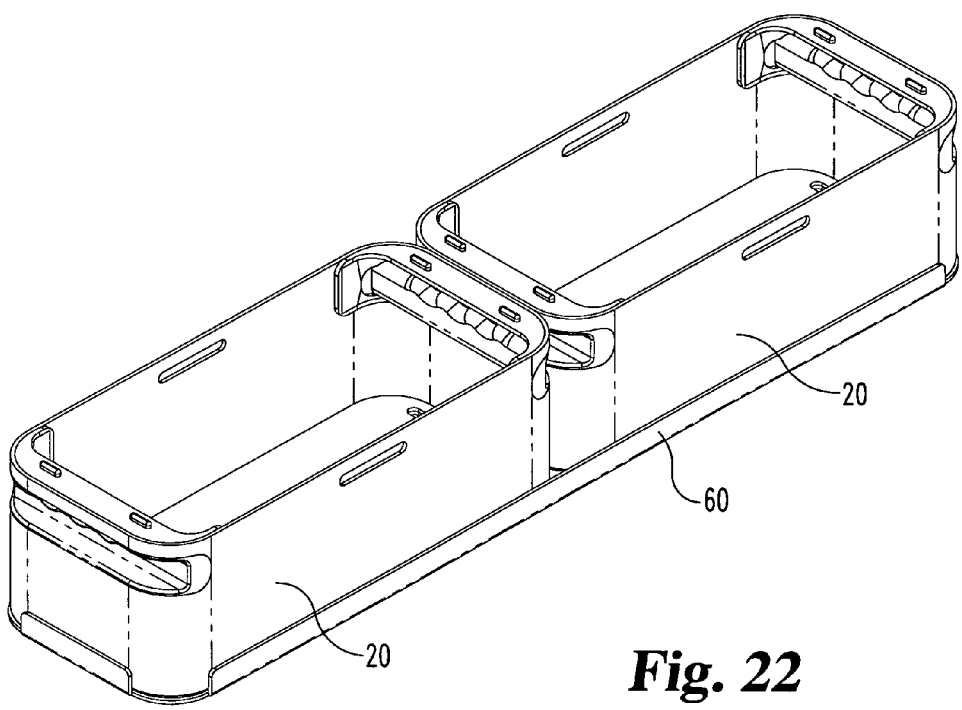
FIG. 22 is a perspective view of the FIG. 21 combination, as assembled.
Figure 23:
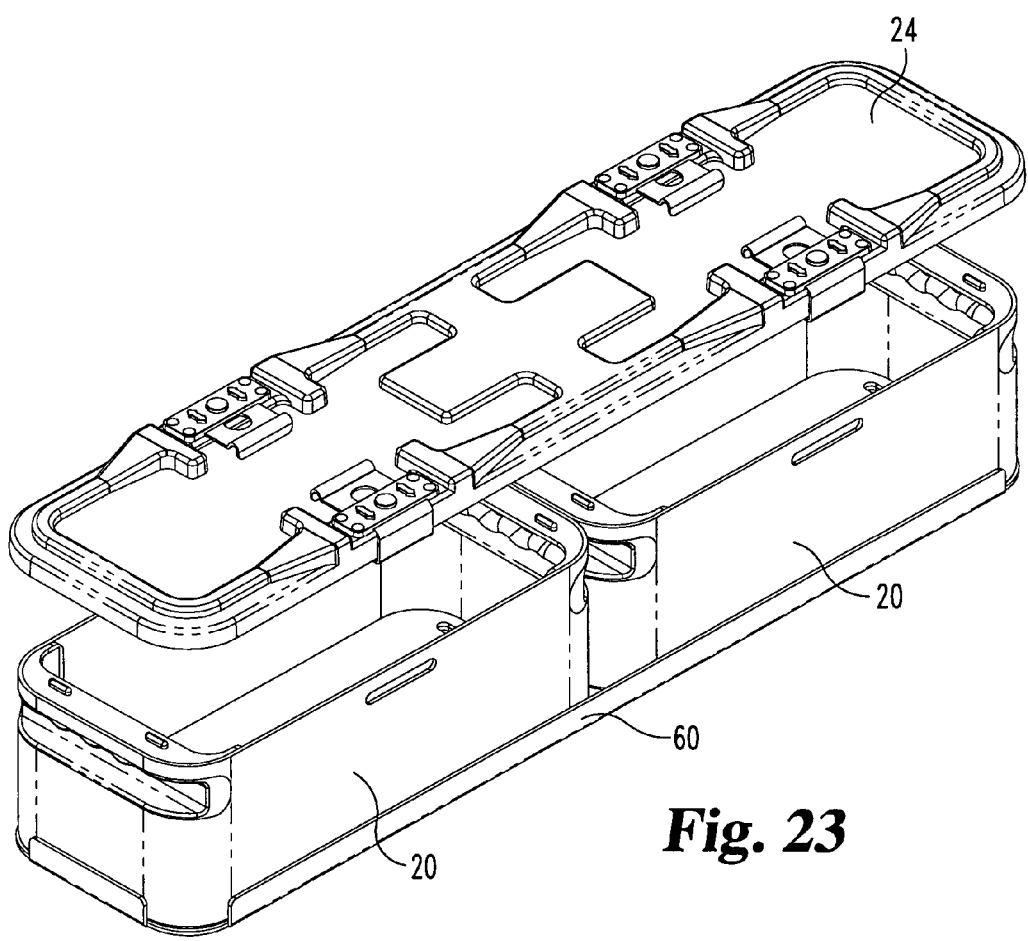
FIG. 23 is an exploded, perspective view of the FIG. 22 assembly with a closing lid.

FIGS. 21-23 illustrate the use of support plate 60 for the tray arrangement of FIGS. 7 and 8. The exploded view of FIG. 21 illustrates the alignment of the support plate 60 to be sure that its raised edge lips 60a fit around the outer periphery of the two modular trays 20 in their end-to-end orientation. The threaded fasteners 65 thread into both trays to securely attach the support plate 60 (see FIG. 22). The case assembly is completed by lid 24, see FIG. 23. Consistent with the modular tray concept disclosed herein and the desire for maximum versatility, lid 24 is also used for tray 21 and the pair of slide latch slots of tray 21 have the same location as when two trays 20 are placed in this end-to-end arrangement.

Figure 24:
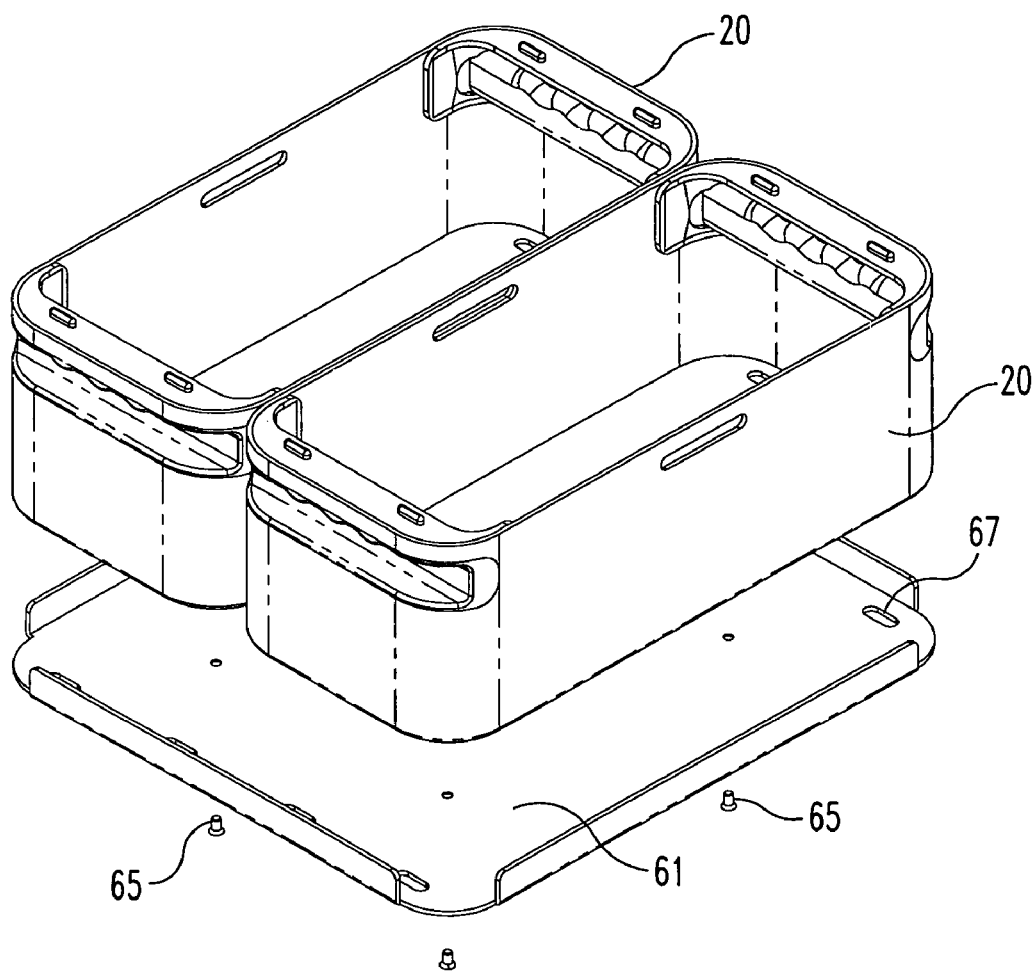
FIG. 24 is an exploded view of a support plate and two modular trays arranged for assembly by mechanical fasteners.
Figure 25:
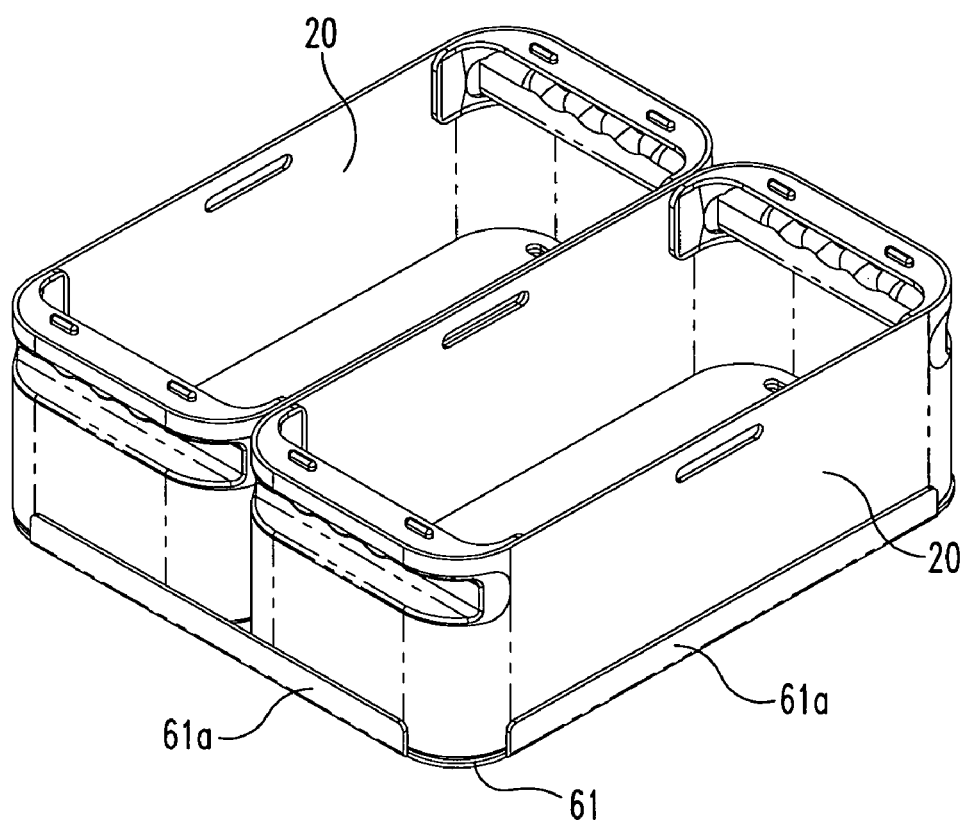
FIG. 25 is a perspective view of the FIG. 24 combination, as assembled.
Figure 26:
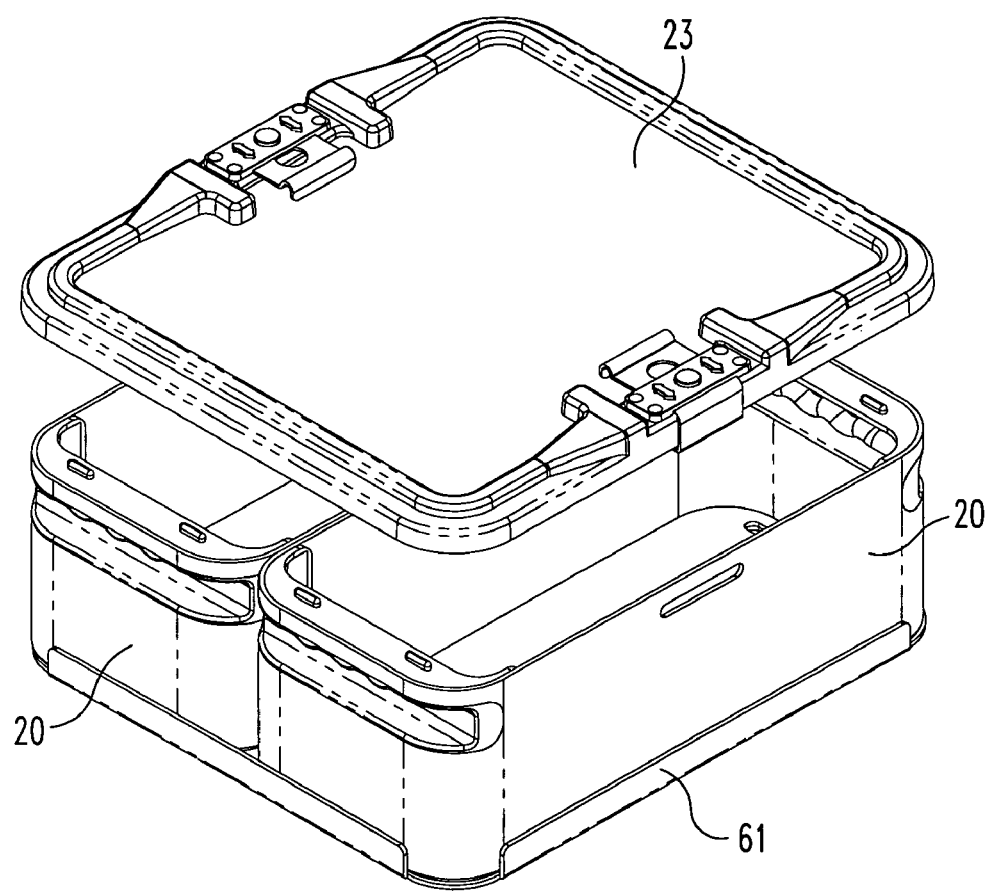
FIG. 26 is an exploded, perspective view of the FIG. 25 assembly with a closing lid.
Figure 27:
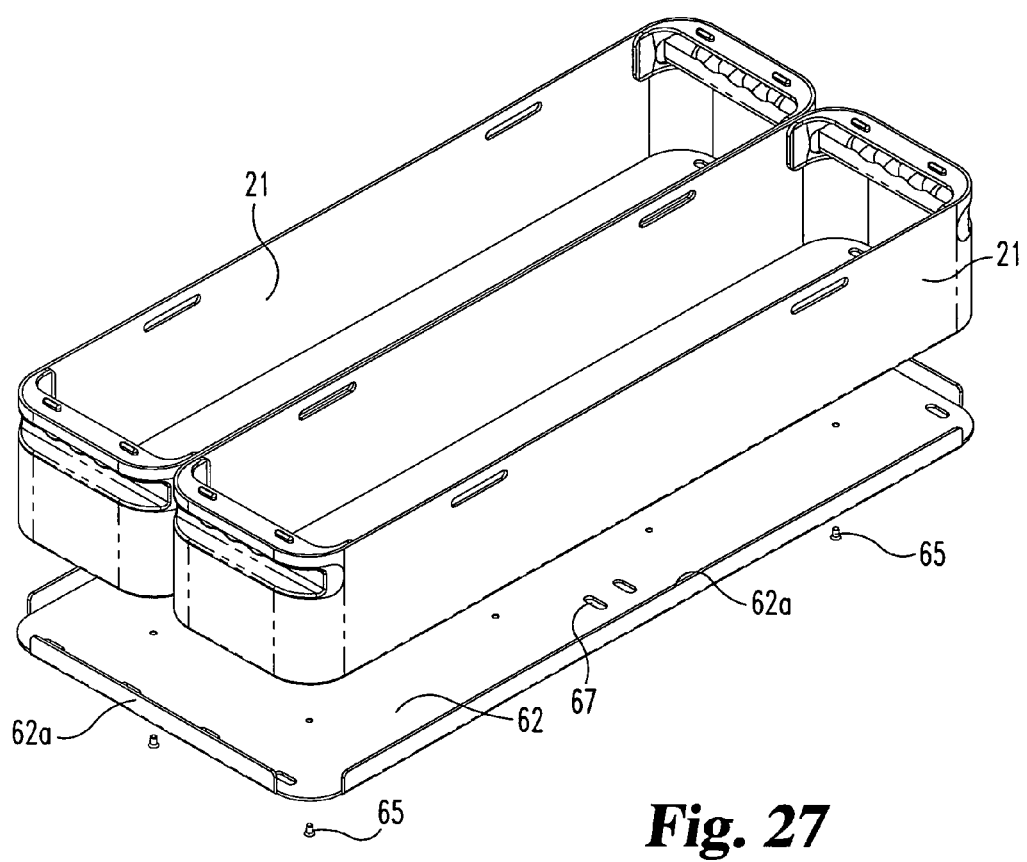
FIG. 27 is an exploded view of a support plate and two modular trays arranged for assembly by mechanical fasteners.
Figure 28:
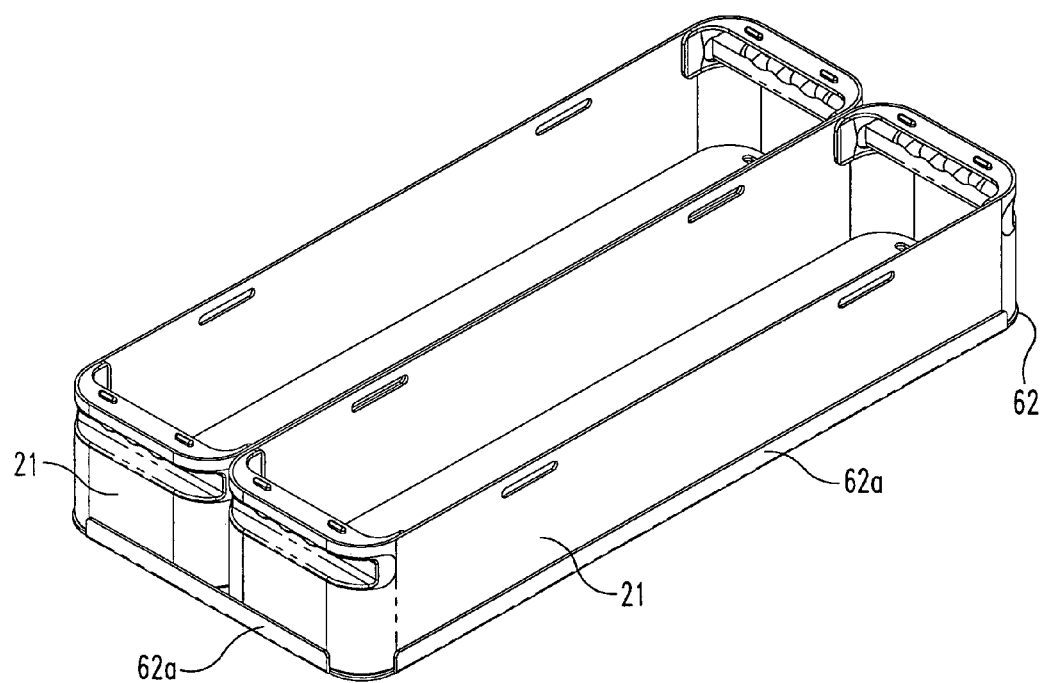
FIG. 28 is a perspective view of the FIG. 27 combination, as assembled.
Figure 29:
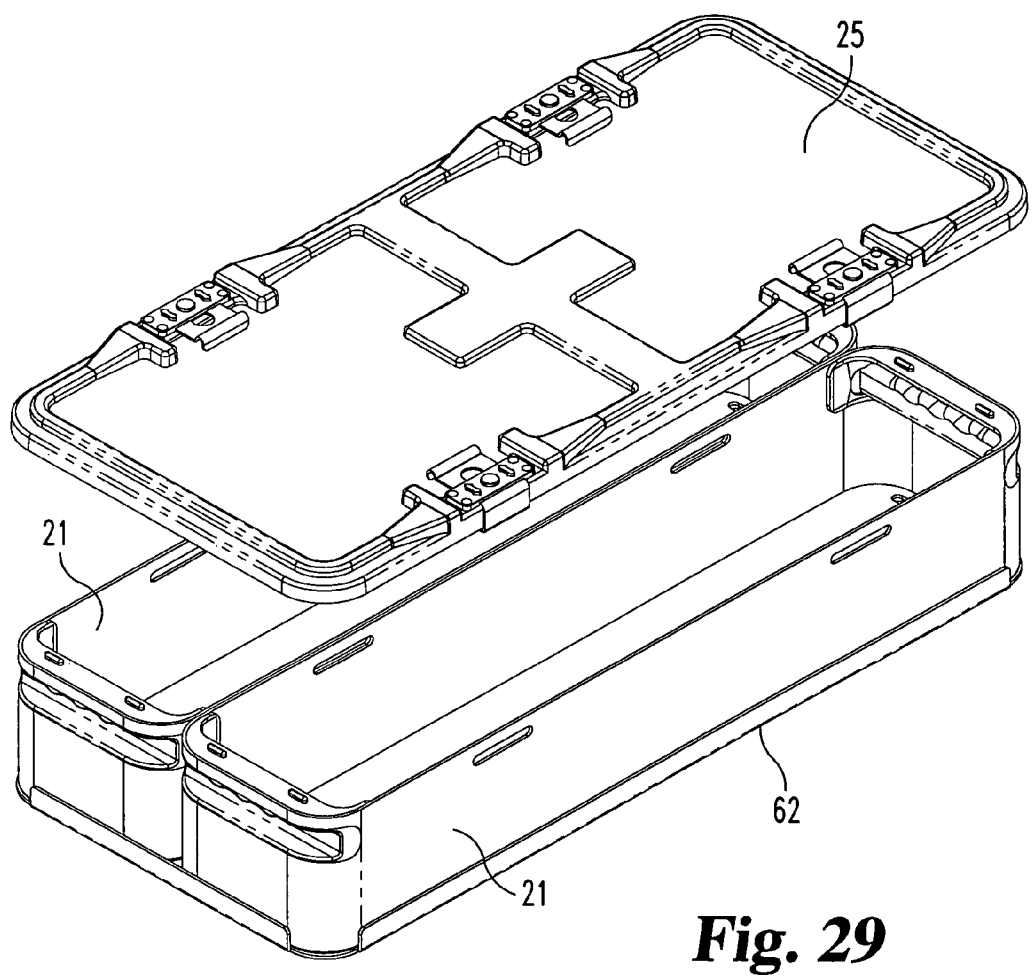
FIG. 29 is an exploded, perspective view of the FIG. 28 assembly with a closing lid.
Figure 30:
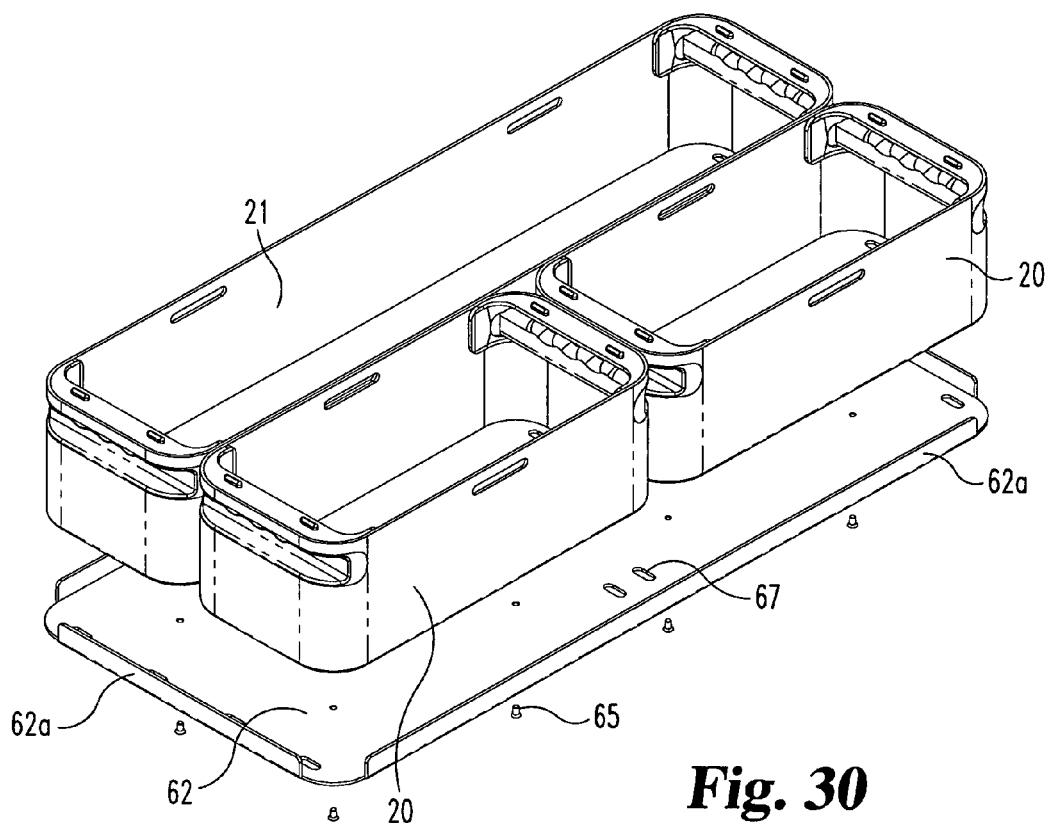
FIG. 30 is an exploded view of a support plate and three modular trays arranged for assembly by mechanical fasteners.
Figure 31:
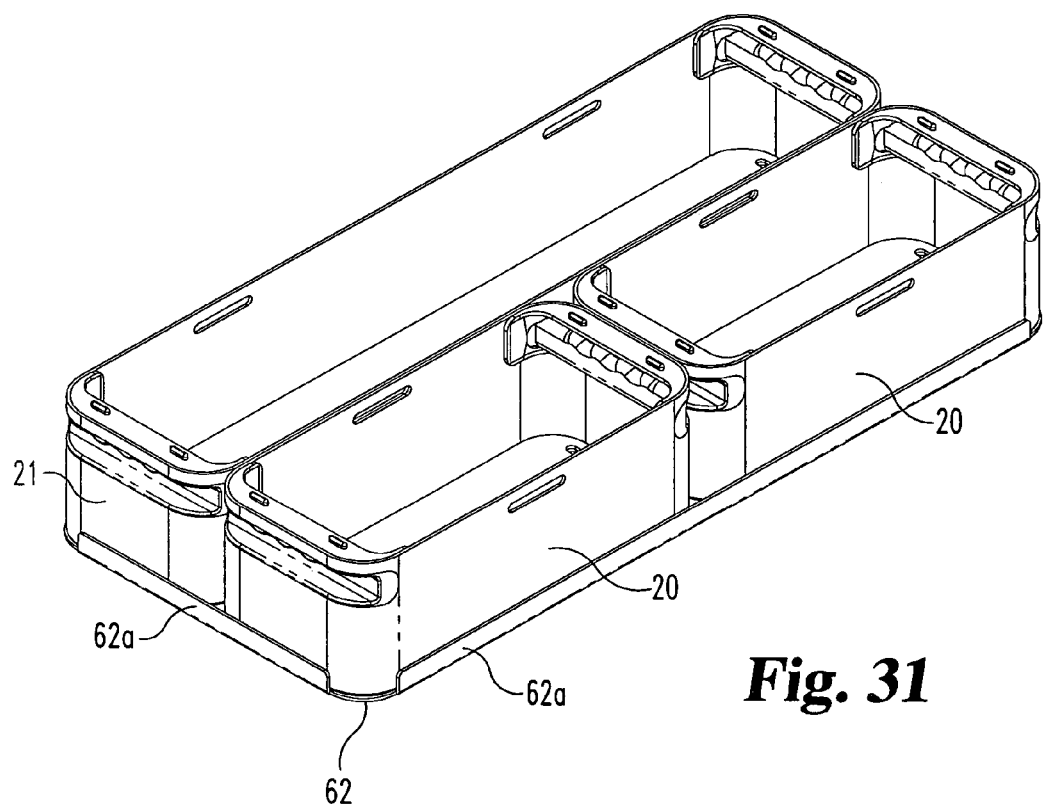
FIG. 31 is a perspective view of the FIG. 30 combination, as assembled.
Figure 32:
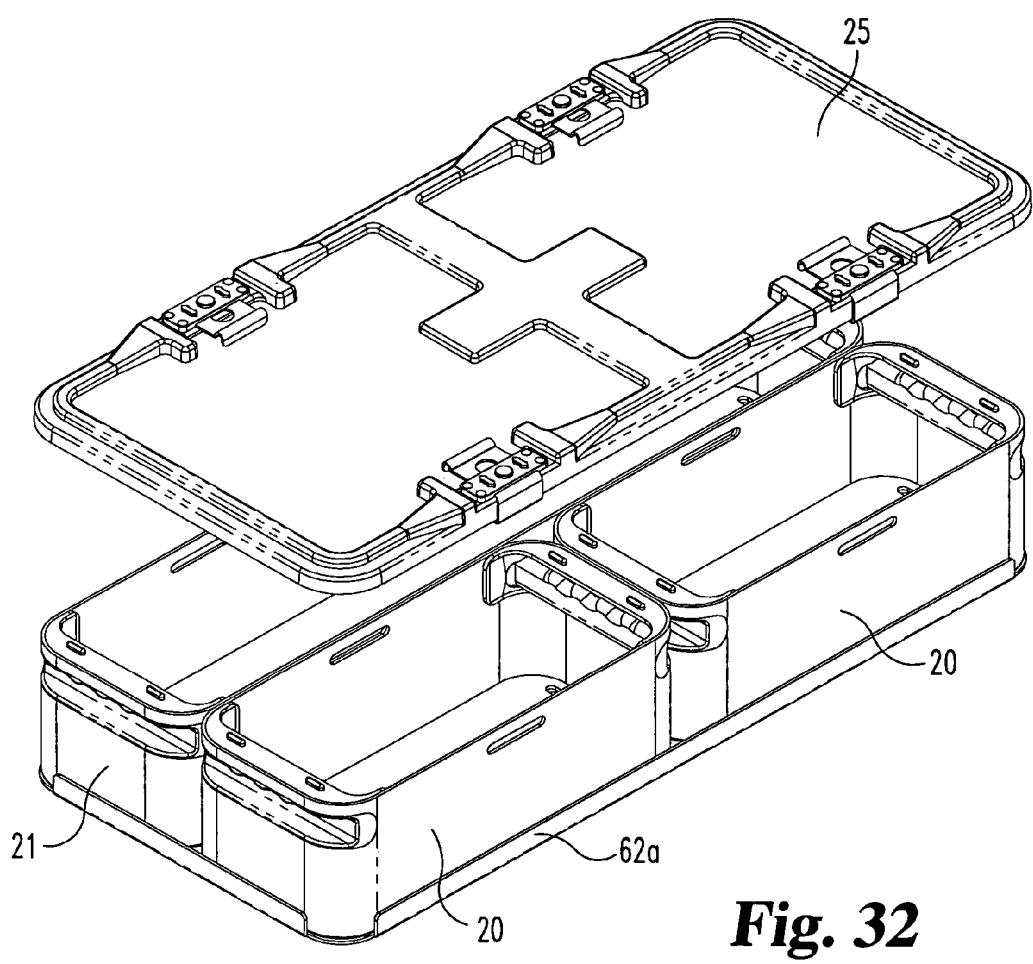
FIG. 32 is an exploded, perspective view of the FIG. 31 assembly with a closing lid.
Figure 33:
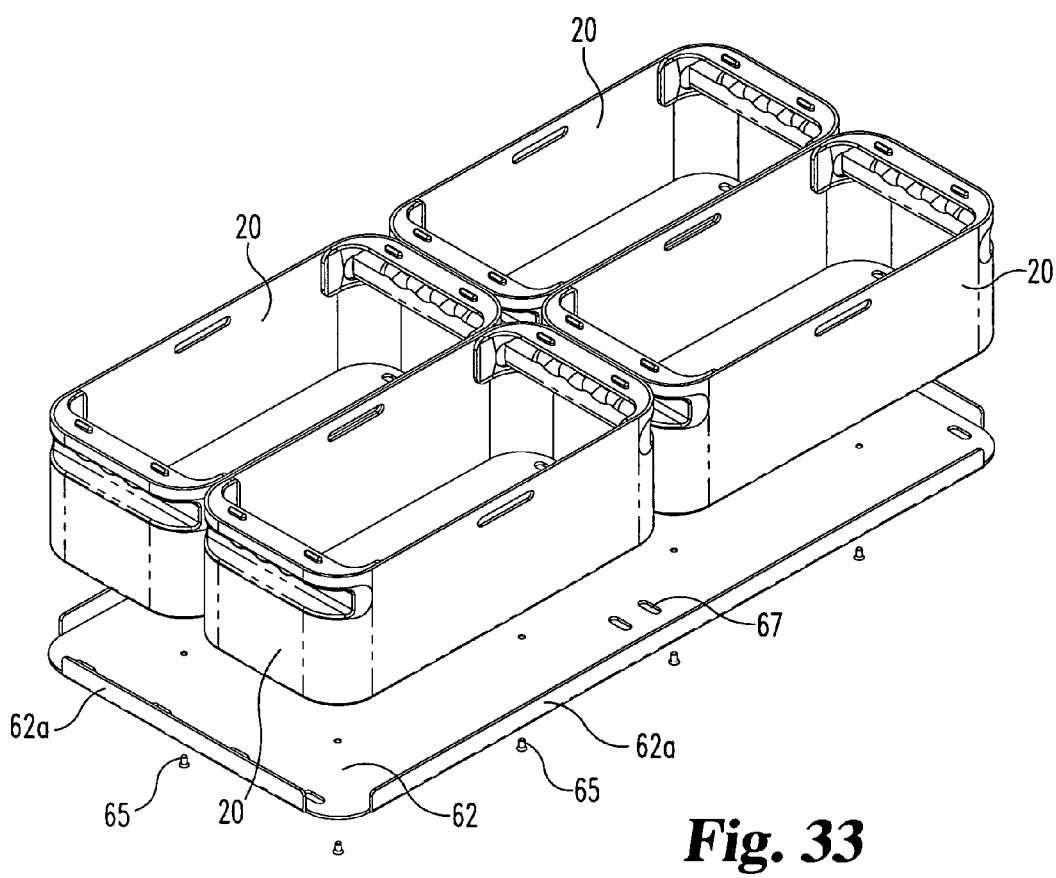
FIG. 33 is an exploded view of a support plate and four modular trays arranged for assembly by mechanical fasteners.
Figure 34:
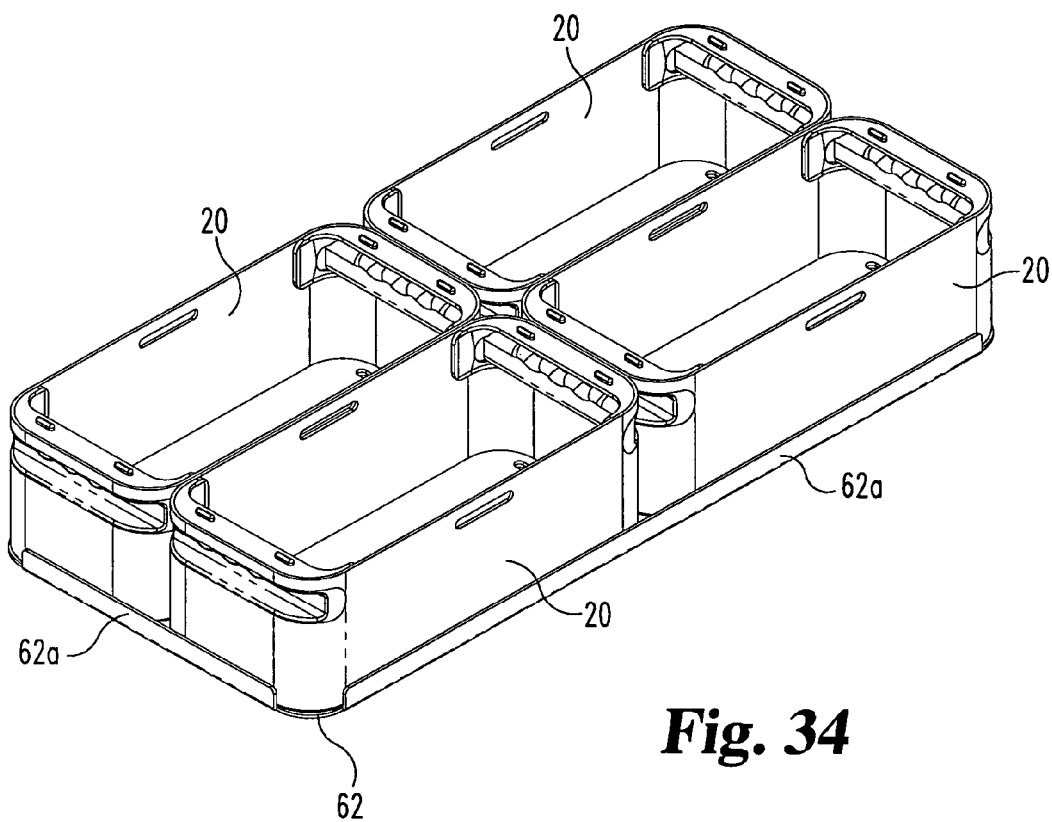
FIG. 34 is a perspective view of the FIG. 33 combination, as assembled.
Figure 35:
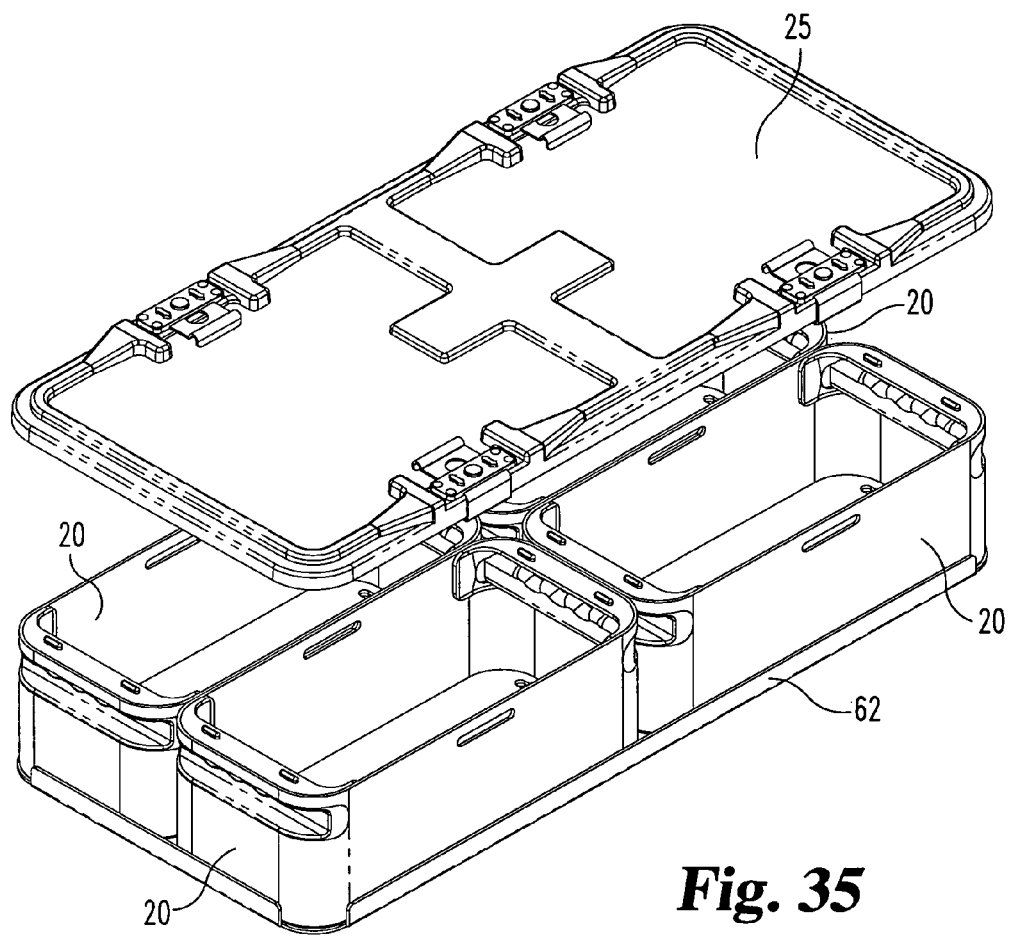
FIG. 35 is an exploded, perspective view of the FIG. 34 assembly with a closing lid.

FIGS. 24-35 show other modular tray arrangements with the required and cooperating support plates and lids. In each instance, the lids and support plates have a virtually identical peripheral size and shape. FIGS. 24-26 correspond to the modular tray arrangement of FIGS. 9 and 10. FIGS. 27-29 correspond to the modular tray arrangement of FIGS. 11 and 12. FIGS. 30-32 correspond to the modular tray arrangement of FIGS. 13 and 14. FIGS. 33-35 correspond to the modular tray arrangement of FIGS. 15 and 16.

Figure 36:
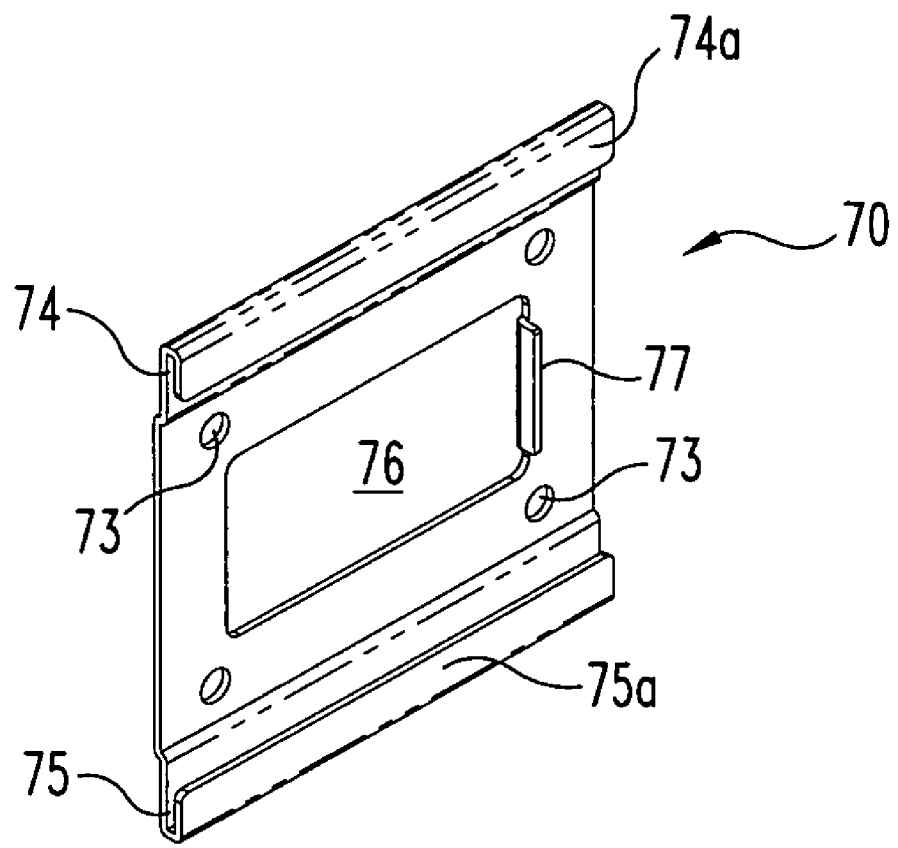
FIG. 36 is a perspective view of a female clip constructed and arranged to be riveted to a modular tray as one part of a mechanical combination for connecting together two trays.
Figure 37:
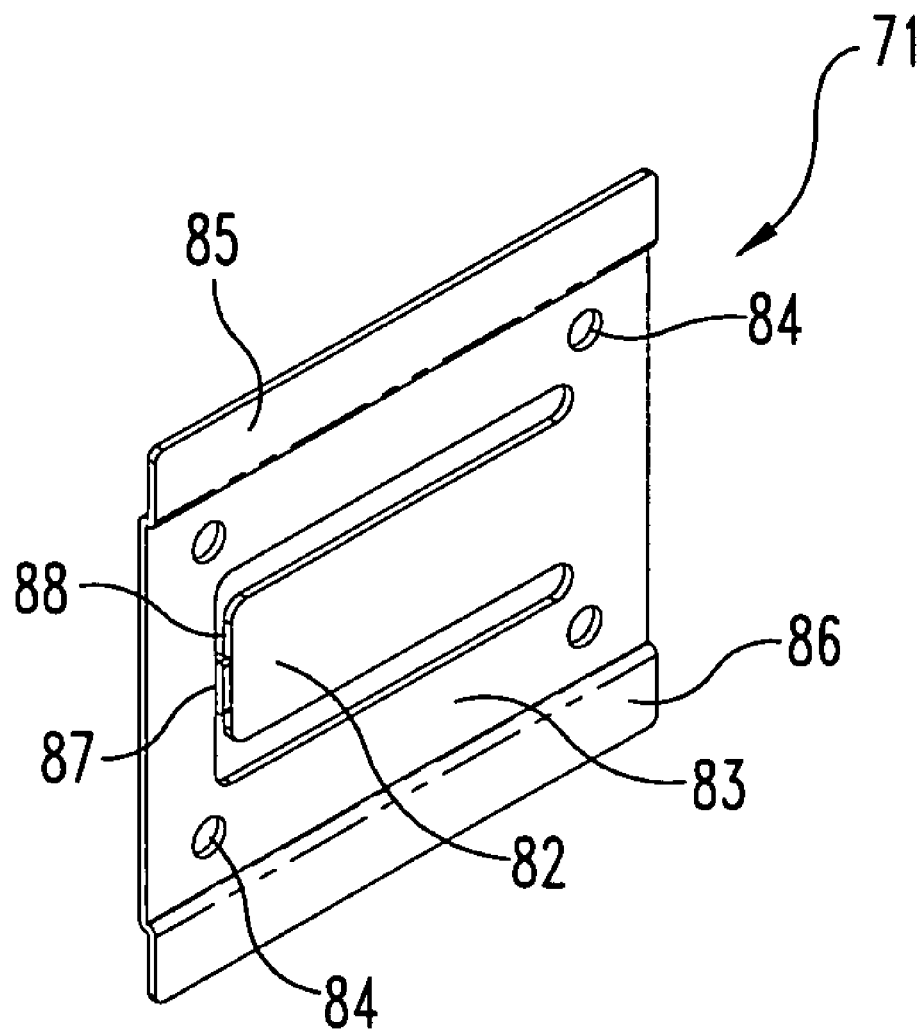
FIG. 37 is a perspective view of a male clip providing the cooperating component for the FIG. 36 clip.
Figure 38:
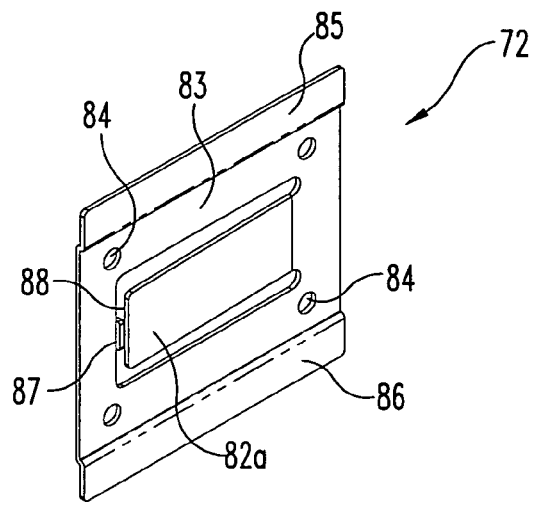
FIG. 38 is a perspective view of an alternative male clip design suitable for use with the FIG. 36 clip according to the present invention.

In the context of the present invention, it has been explained that by the use of cooperating male and female forms, the modular trays, as disclosed herein, can be connected together with a snap-fit. One embodiment for this snap-fit construction is illustrated in FIGS. 36-44. Referring to FIG. 36, female clip 70 is illustrated, while FIG. 37 illustrates one style of male clip 71 and FIG. 38 illustrates another style of male clip 72. Each of these male clips are suitable for connection with female clip 70 in order to securely connect one modular tray to another modular tray, whether by a side-by-side arrangement or by an end-to-end arrangement. If only one style of male clip is to be used, it would be preferable to use male clip 72, since it provides a snap-fit connection. Male clip 71 provides only a sliding fit connection with female clip 70.

Figure 39:
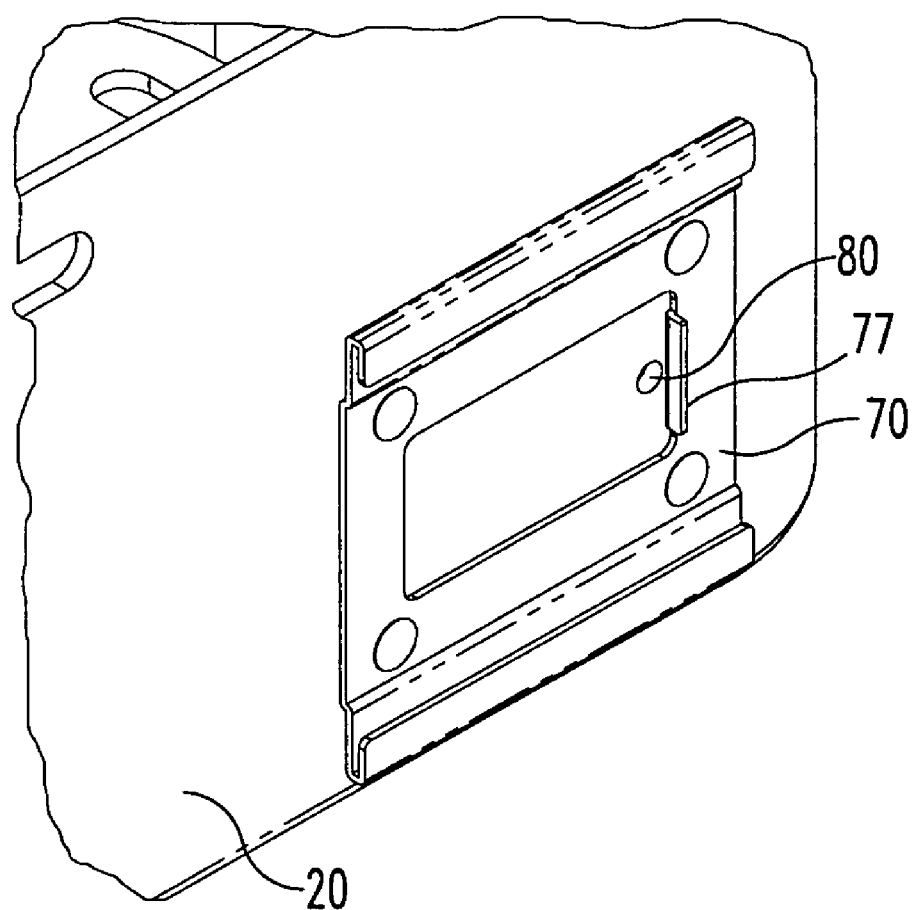
FIG. 39 is a partial, perspective view of the FIG. 36 clip, as riveted to a tray.
Figure 40:
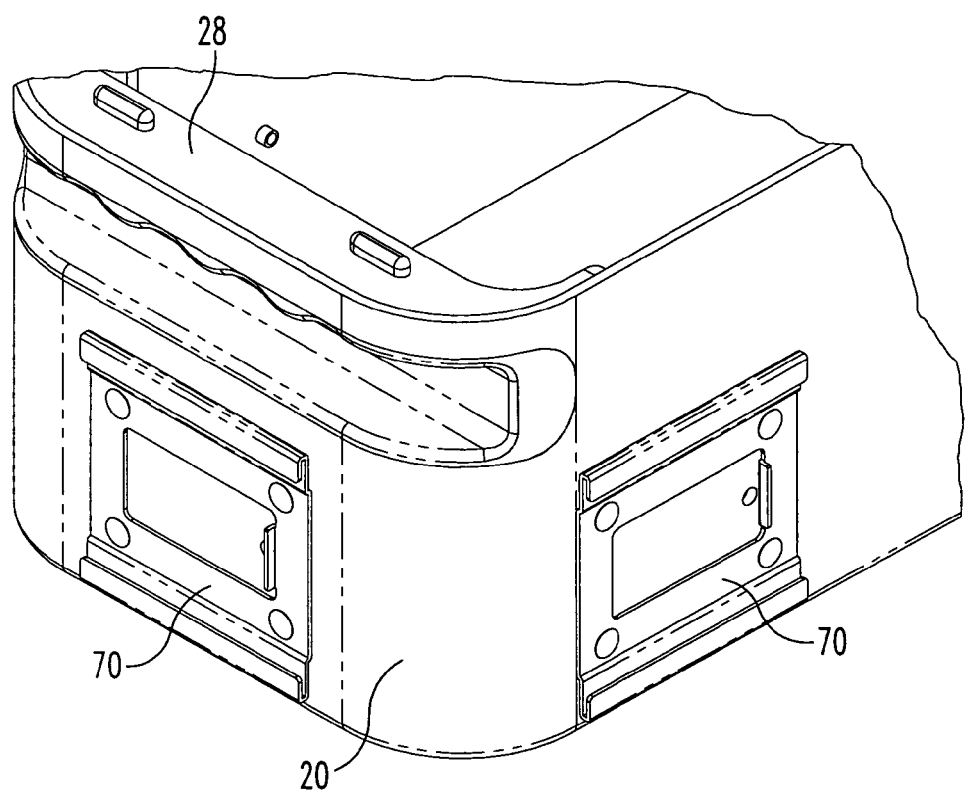
FIG. 40 is a partial, perspective view of two FIG. 36 clips, as riveted to a side wall and an end wall of a tray.

Clip 70 includes four clearance holes 73 for riveting clip 70 to a side wall or end wall of a selected modular tray. An upper channel 74 is formed in part by lip 74a. A lower channel 75 is formed in part by lip 75a. The upper channel 74 and lower channel 75 are constructed and arranged to receive upper and lower flanges of clip 71 or of clip 72, depending on which male clip has been selected for the tray-to-tray connection. The rectangular center opening 76 includes an abutment stop 77. The riveted connection of clip 70 to a modular tray is illustrated in FIG. 39. The clearance hole 80 is to be used for the insertion of a pin or rod or similar implement in order to release the male clip 72 from the female clip 70 for disconnecting the snapped together modular trays. Since clip 71 does not involve a snap-fit connection, only a sliding fit, a clearance hole 80 is not required at the site of any clip 71, only at the site of clip 72. However, for maximum versatility and to provide complete options in terms of clip selection, providing holes 80 at all locations is preferable so that either clip 71 or clip 72 can be selected and used at each connecting site in cooperation with clip 70. A pair of clips 70 are illustrated in FIG. 40, one clip 70 is riveted to a side wall of a modular tray and the other clip 70 is riveted to an end wall of that same modular tray.

Referring now to FIGS. 37 and 38, male clips 71 and 72 are virtually identical, their only difference being the angle or incline of tongues 82 and 82*a* relative to the surrounding panel 83. Panel 83 defines four rivet holes 84 and longitudinal upper and lower flanges 85 and 86, respectively, are configured on opposite sides of panel 83. The rectangular (three-sided) opening that helps to define tongue 82 (and tongue 82*a*) includes a small abutment tab 87 spaced apart from the tip (free end) 88 of tongue 82 (and tongue 82*a*). As is illustrated, clip 71 includes a tongue 82 that is substantially flush with panel 83. Clip 72 includes a tongue 82*a* that is raised slightly, and this tongue 82*a* springs down as it slides over abutment stop 77 during any sliding in or sliding out movement as the two modular trays are connected to each other. Once tongue 82*a* clears the abutment stop 77, the tongue 82*a* snaps back into an interlocking combination with clip 70. As explained, it is clip 72 with tongue 82*a* that creates a snap-fit assembly with a cooperating female clip 70. Clip 71 creates only a sliding fit by means of upper and lower flanges 85 and 86 sliding into upper and lower channels 74 and 75. In this regard, it is to be understood that the upper and lower channels are substantially straight and the clearance space within the channel is sufficiently wide to receive the upper and lower flanges 85 and 86, based on their material thickness with a sliding fit, but still with a relatively tight fit so as to maintain some rigidity with regard to the connected modular trays.

Figure 41:
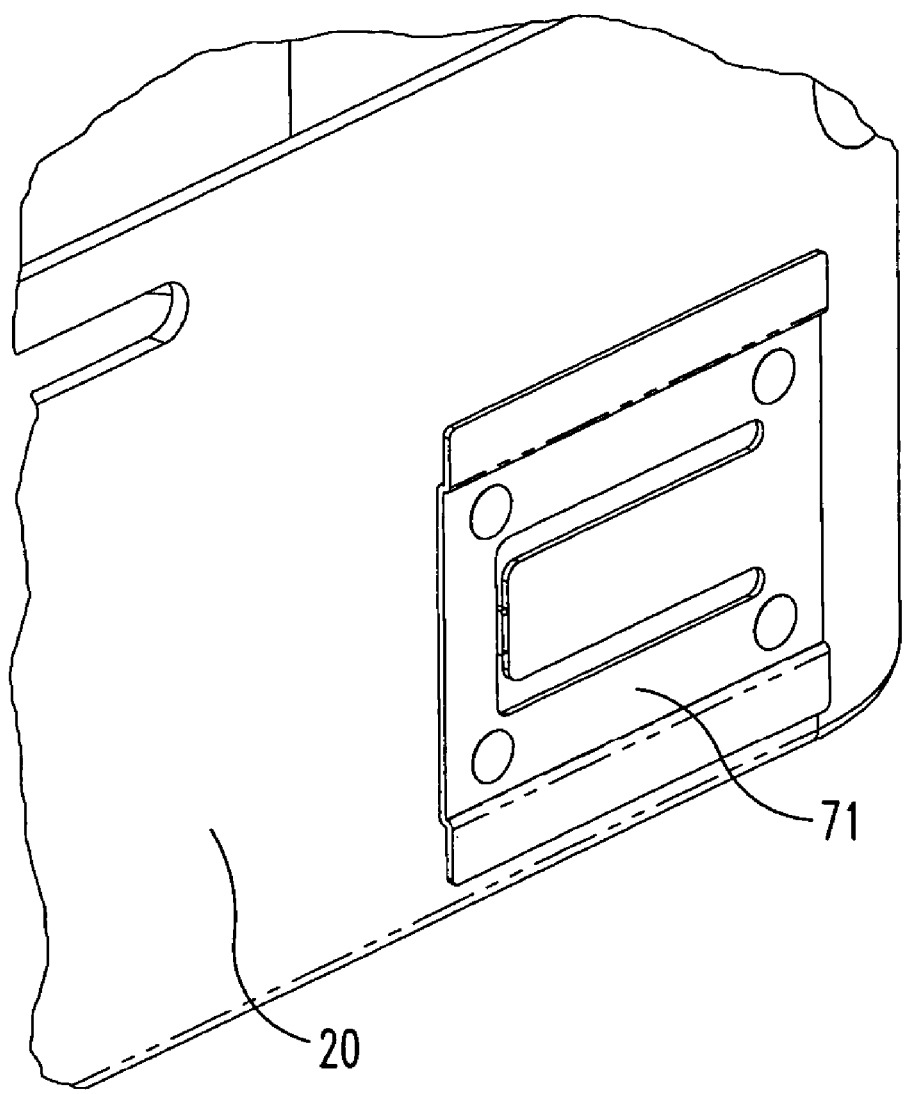
FIG. 41 is a partial, perspective view of the FIG. 37 clip, as riveted to a tray.
Figure 42:
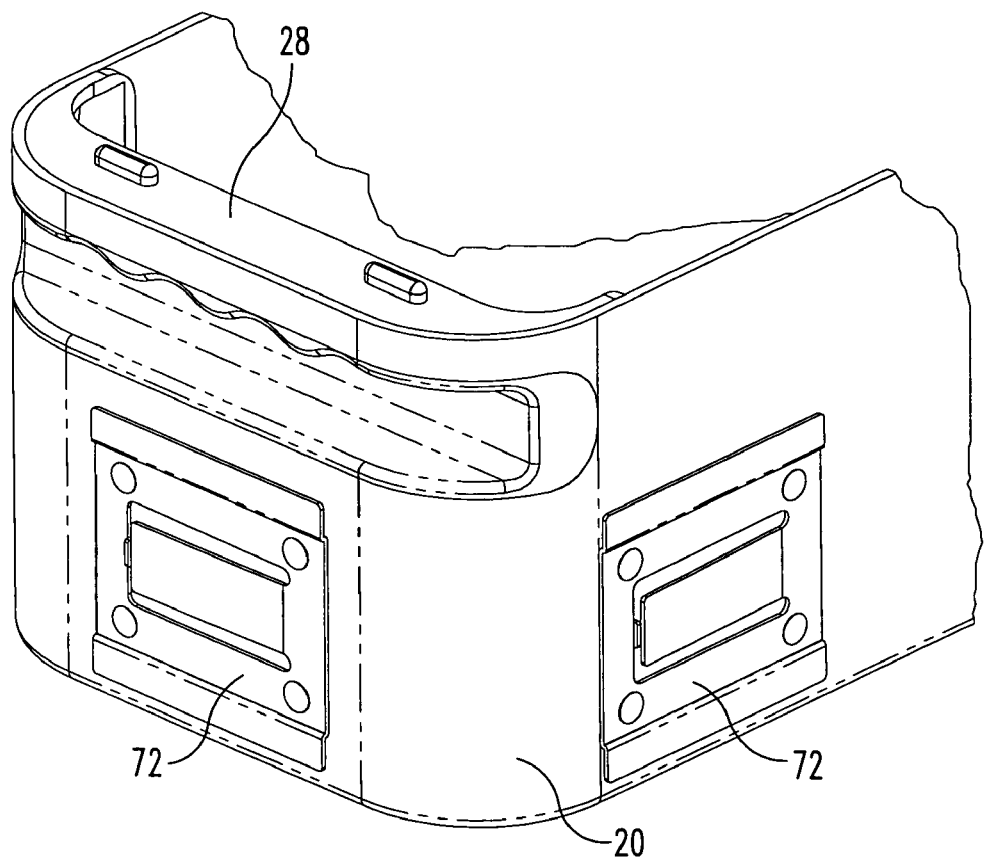
FIG. 42 is a partial, perspective view of two FIG. 38 clips, as riveted to a side wall and to an end wall of a tray.

FIG. 41 illustrates the riveted attachment of male clip 71 to a modular tray, in this example tray 20. It is to be understood that the virtually identical construction of clips 71 and 72 would cause the attachment of clip 72 to be, and look, virtually identical to the attachment of clip 71. In FIG. 42, one clip 72 is attached to a side wall of modular tray 20 and a second clip 72 is attached to an end wall of that same modular tray. If a snap-fit connection to female clip 70 is desired at a particular location, then male clip 72 is used at that location.

Figure 43:
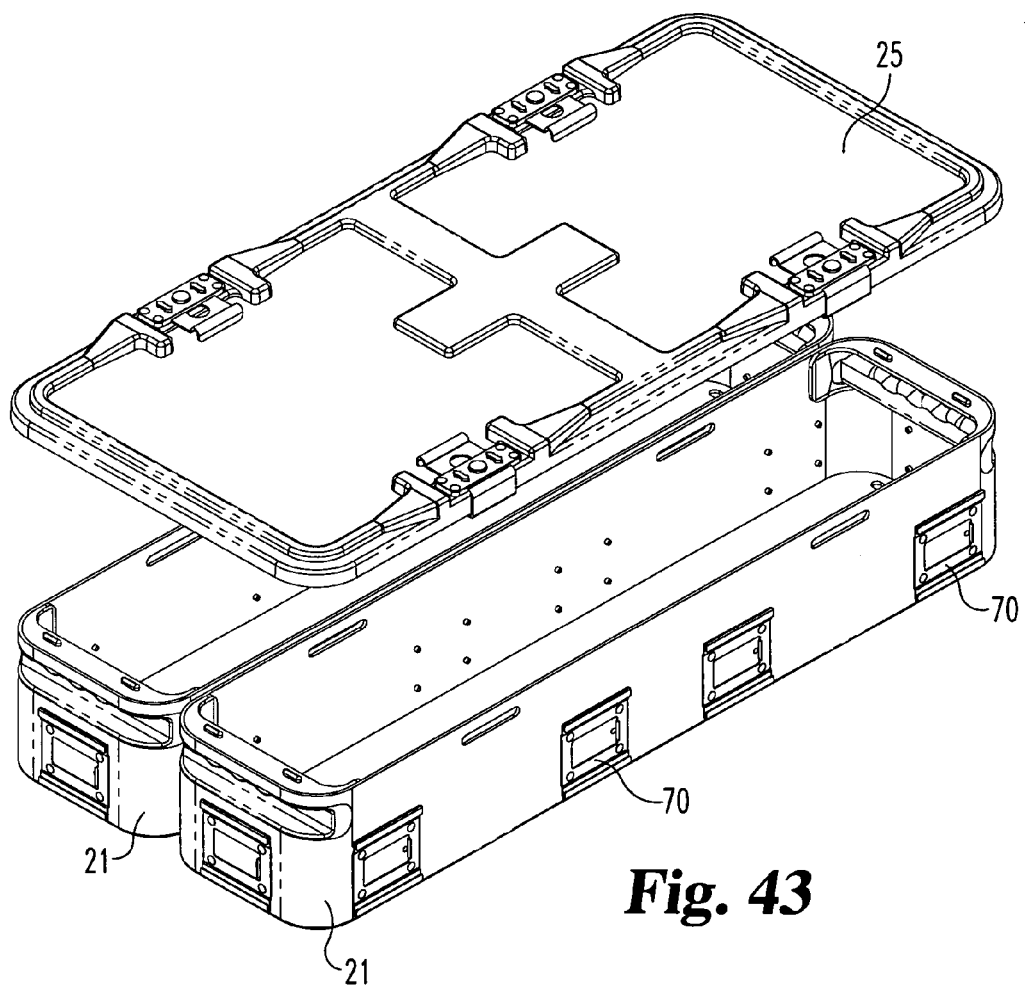
FIG. 43 is an exploded view of a two-tray and lid combination showing a plurality of the FIG. 36 clips.
Figure 44:
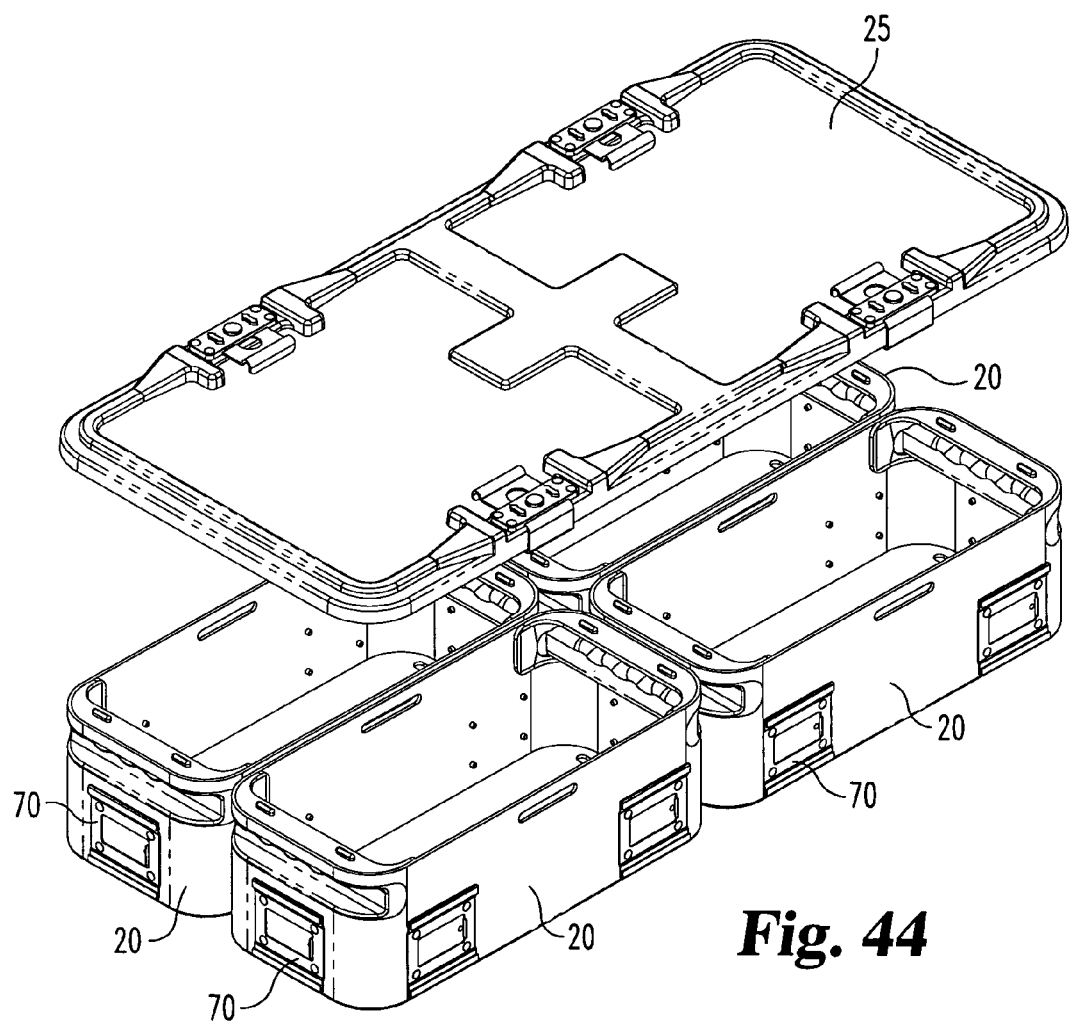
FIG. 44 is an exploded view of a two-tray and lid combination showing a plurality of the FIG. 36 clips.

FIG. 43 illustrates the connection of two trays 21 to each other using a spaced-apart series of four female clips 70 on one side panel of one tray and a correspondingly spaced-apart series of four male clips 71 (and/or 72) on one side panel of the connecting tray. In FIG. 44, four trays 20 are connected, the locations of connection are both side-to-side as well as end-to-end.

It is to be understood that the connecting together of two trays by this technique of using female clip 70 and male clip 71 and/or 72 requires one style of clip on one tray and the complementing style of clip on the other tray that is to be connected, noting that these clip arrangements need to be on facing or abutting side walls or end walls of the corresponding modular trays. For example, in FIG. 43, if the front tray (referring now to orientation on the drawing sheet) and the partially hidden tray 21 are identical, then the abutting side wall of the partially hidden tray has a construction identical to the exposed side wall of the front tray, specifically that abutting side wall includes four female clips 70. In order to securely and rigidly connect these two trays together by the selected technique using male and female clips, the opposite side wall (the abutting side wall) of the front tray 21 must include at least one male clip, either clip 71 or clip 72, preferably four male clips would be used for maximum strength and rigidity, so as to complement and connect to the four female clips 70. For a snap-fit connection, at least one clip 72 must be used.

Figure 38A:
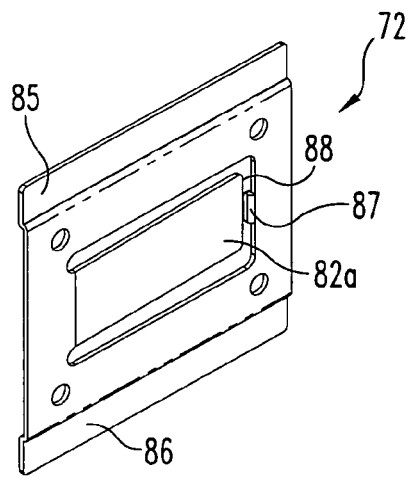
FIG. 38A is a perspective view of the FIG. 38 clip as turned for a proper orientation for a snap-fit assembly with the FIG. 36 clip.
Figure 38B:
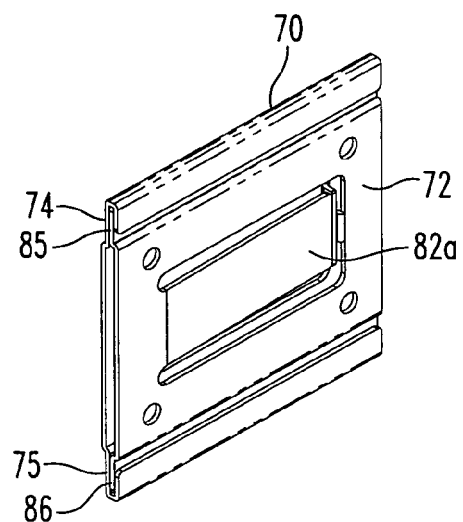
FIG. 38B is a perspective view of the snap-fit assembly of the FIG. 36 clip and of the FIG. 38 clip.

Referring further to FIGS. 36 and 38, the sliding interfit between clip 70 and clip 72 requires the two flanges 85 and 86 of clip 72 to slide into the two cooperating channels 74 and 75 of clip 70. Although the FIG. 38 orientation needs to be turned in order to achieve the correct orientation for connecting these two modular trays, the interconnection should be fairly easy to follow, based on the drawing illustrations provided. To help with this understanding, the FIG. 38A illustration positions clip 72 in the proper orientation for its snap-fit assembly with clip 70. By flipping over the clip 72 of FIG. 38 so that the free end of tongue 82*a* is to the right side of the page, as shown in FIG. 38A, this orients the FIG. 36 and FIG. 38 clips as they would be oriented with their corresponding trays facing each other. As clip 72 slides into clip 70, the abutment stop 77 pushes on tongue 82*a*, causing it to deflect. This action continues until the free end 88 clears the abutment stop 77, at which point the tongue 82*a* springs back and assumes a position of interlock relative to stop 77. This is how the referenced snap-fit assembly is achieved. This clip combination is illustrated in FIG. 38B. Any sliding movement of one tray relative to the other in the reverse direction causes tongue 82*a* to abut up against stop 77. This is why tongue 82*a* has to be pushed out (reference hole 80) in order to disconnect the two trays. Tab 87 is a safety feature that prevents sliding one clip too far relative to the other clip. Tab 87 is positioned at the opposite side of stop 77 as a way to control or limit the amount of sliding travel of one tray relative to the other tray. Tab 87 also prevents trying to disconnect the two trays by sliding them in the "wrong" direction.

Figure 45:
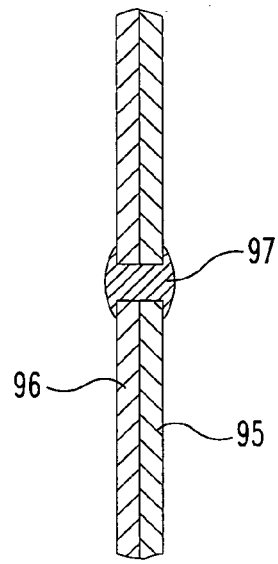
FIG. 45 is an end elevational view, in full section, of two tray side walls, as connected together using a rivet.
Figure 46:
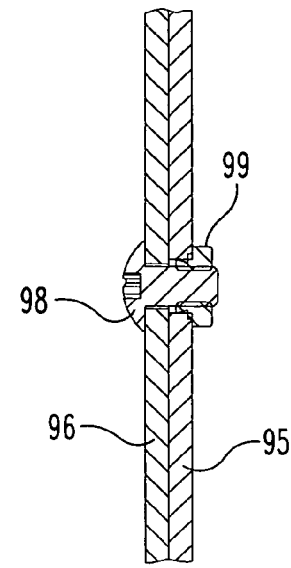
FIG. 46 is an end elevational view, in full section, of two tray side walls being connected by a screw and nut combination.
Figure 47:
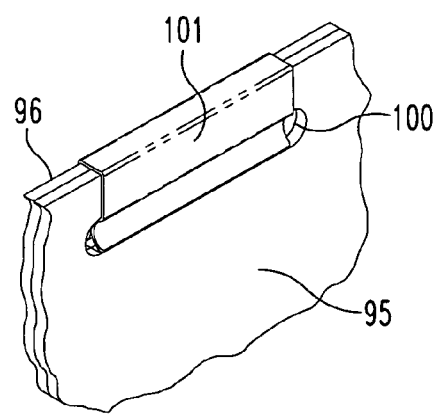
FIG. 47 is a partial, perspective view of two tray side walls being connected by a spring clip.
Figure 48:
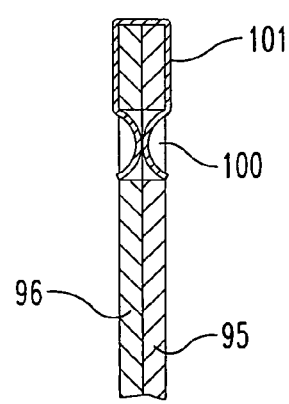
FIG. 48 is an end elevational view, in full section, of the FIG. 47 combination.
Figure 49:
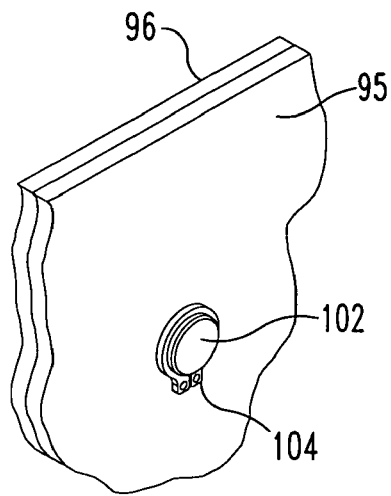
FIG. 49 is a partial, perspective view of two tray side walls connected together by a pin and retaining ring combination.
Figure 50:
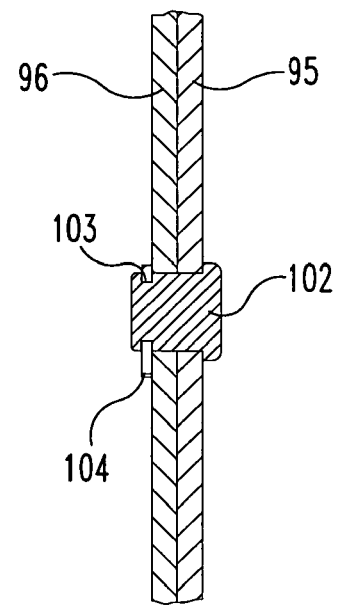
FIG. 50 is an end elevational view, in full section, of the FIG. 49 combination.
Figure 51:
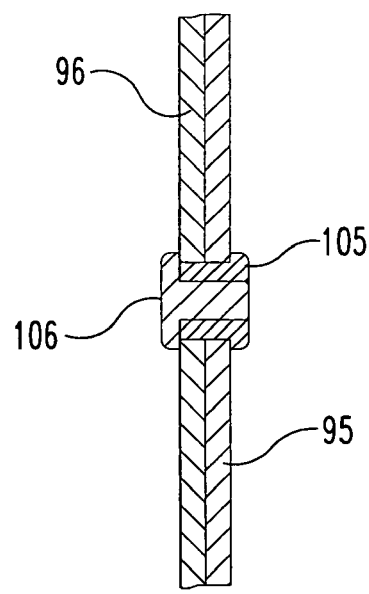
FIG. 51 is an end elevational view, in full section, of two tray side walls being connected by a hollow pin and post combination.

While the support plates 60, 61 and 62 and the female and male clips 70, 71, and 72 represent the preferred connection structures for securely connecting one modular tray to another, other connection structures are contemplated. Referring now to FIGS. 45-51, these other connection structures are illustrated. In each illustration, one tray 20, sidewall 95 (or end wall) is placed up against a cooperating tray 20 side wall 96 (or end wall). In FIG. 45, a rivet 97 is disclosed. In FIG. 46, a threaded fastener (screw) 98 and threaded nut 99 are used. In FIGS. 47 and 48 an oblong slot 100 in each side wall 96 and 97 receives a spring clip 101. In FIGS. 49 and 50 a headed fastener 102 includes a retaining ring groove 103 at one end that receives a retaining ring 104. In FIG. 51, a hollow, headed fastener 105 receives a press-fit headed pin 106 that is inserted into the hollow interior of fastener 105.

While the invention has been illustrated and described in detail in the drawings and foregoing description, the same is to be considered as illustrative and not restrictive in character, it being understood that only the preferred embodiment has been shown and described and that all changes and modifications that come within the spirit of the invention are desired to be protected.

The invention claimed is:

1. A modular tray and lid combination for constructing a containment case, the modular tray and lid combination comprising:
    a) a plurality of modular trays, each modular tray including a pair of side walls and a pair of end walls cooperating to define an upper opening, wherein each of the modular trays includes means for connecting the modular tray with at least one other modular tray of the plurality of modular trays; and
    b) a single closing lid constructed and arranged to be simultaneously supported by each modular tray of the plurality of modular trays for closing their upper openings, and then latchable thereto; and
    c) wherein the single closing lid is removable from the plurality of modular trays by unlatching so that every one of the modular trays is only either open with the lid removed from each of their upper openings or closed with the lid closing each of their upper openings.

2. The modular tray and lid combination of claim 1 which further includes at least one slide latch assembled to the closing lid and being constructed and arranged to interfit into at least one modular tray.

3. The modular tray and lid combination of claim 2 wherein at least one of the side walls and end walls defines a slot for receiving a portion of the at least one slide latch.

4. The modular tray and lid combination of claim 1 wherein the means for connecting includes a support plate that is assembled to at least one of the plurality of modular trays.

5. The modular tray and lid combination of claim 1 wherein the plurality of modular trays includes two modular trays arranged and connected side-by-side.

6. The modular tray and lid combination of claim 3 wherein the slot of one modular tray is oppositely positioned relative to the slot of another modular tray.

7. The modular tray and lid combination of claim 6 which further includes a second slide latch for a total of at least two slide latches, wherein one of the modular trays receives a portion of a first one of the slide latches and the other modular tray receives a portion of the second slide latch.

8. The modular tray and lid combination of claim 1 wherein the plurality of modular trays includes two modular trays arranged so as to be connectable to each other.

9. The modular tray and lid combination of claim 7 wherein the slot of one modular tray is oppositely positioned relative to the slot of the other modular tray.

10. The modular tray and lid combination of claim 2 wherein the plurality of modular trays includes four modular trays, wherein a first modular tray is arranged and connected to a second modular tray side-by-side and to a third modular tray end-to-end and wherein a fourth modular tray is arranged and connected to the second modular tray end-to-end and to the third modular tray side-by-side.

11. The modular tray and lid combination of claim 10 wherein the first and third modular trays each include an outer side wall that defines a first slot and wherein the second and fourth modular trays each include an outer side wall that defines a second slot.

12. The modular tray and lid combination of claim 11 which further includes a second slide latch for a total of at least two slide latches, wherein one of the first and third modular trays receives a portion of a first one of the slide latches and one of the second and fourth modular trays receives a portion of the second slide latch.

13. The modular tray and lid combination of claim 1 wherein there are a pair of handles assembled to each modular tray of the plurality, each handle including a raised form constructed and arranged for the stacking of modular trays, and wherein each modular tray of the plurality includes a bottom panel defining an aperture, each aperture being constructed and arranged to receive the raised form for the stacking of modular trays.

14. A modular tray and lid combination for constructing a containment case, the modular tray and lid combination comprising:
   a) at least two single modular trays, each having a first length dimension and a width dimension, the at least two single modular trays each including a pair of side walls and a pair of end walls cooperating to define an upper opening, wherein the at least two single modular trays include first means for connecting to another modular tray;
   b) at least one double modular tray having a second length dimension and a width dimension, the second length dimension being approximately twice the first length dimension of each of the at least two single modular trays, wherein the at least one double modular tray includes a pair of side walls and a pair of end walls cooperating to define an upper opening, and wherein the at least one double modular tray includes a second means for connecting to another modular tray, and wherein the at least two single modular trays are connectable to the at least one double modular tray via the first and second means; and
   c) a single closing lid constructed and arranged to be simultaneously supported by the at least two single modular trays and the at least one double modular tray, and then latchable thereto; and
   d) wherein the single closing lid is removable from the at least two single modular trays and the at least one double modular tray by unlatching so that every one of the modular trays is only either open with the lid removed from each of their upper openings or closed with the lid closing each of their upper openings.

15. The modular tray and lid combination of claim 14 which further includes at least one slide latch assembled to the closing lid and being constructed and arranged to interfit into at least one of the single modular trays and the one double modular tray.

16. The modular tray and lid combination of claim 15 wherein at least one of the side walls and end walls defines a slot for receiving a portion of the at least one slide latch.

17. The modular tray and lid combination of claim 14 wherein one of the first and second means for connecting includes a male clip that is assembled to at least one of the modular trays.

18. The modular tray and lid combination of claim 14 wherein the slot of one modular tray is oppositely positioned relative to the slot of one of the other modular trays.

19. A method of creating a containment case from a plurality of modular trays, the method comprising the following steps:
   a) providing a plurality of modular trays, each modular tray including a pair of side walls and a pair of end walls cooperating to define an upper opening, wherein each of the modular trays includes means for connecting the modular tray with at least one other modular tray of the plurality of modular trays;
   b) providing a single closing lid constructed and arranged to be simultaneously supported by each modular tray of the plurality of modular trays for closing their upper openings;
   c) connecting together a plurality of modular trays using the means for connecting, wherein every one of the connected modular trays is open with the lid removed from each of their upper openings;
   d) placing the closing lid on the connected plurality of modular trays so that every one of the modular trays has the lid closing each of their upper openings; and
   e) latching the closing lid to the connected plurality of modular trays for securing the closing lid in a closing position.

20. A modular tray and lid combination for constructing a containment case, the modular tray and lid combination comprising:
   a) a plurality of modular trays, each modular tray including a pair of side walls and a pair of end walls cooperating to define an upper opening;
   b) a support plate constructed and arranged to fit beneath the plurality of modular trays when they are arranged for connection, the support plate contacting each modular tray of the plurality of modular trays; and c) a single closing lid constructed and arranged to be simultaneously supported by each modular tray of the plurality of modular trays for closing their upper openings, and then latchable thereto; and d) wherein the single closing lid is removable from the plurality of modular trays by unlatching so that every one of the modular trays is only either open with the lid removed from each of their upper openings or closed with the lid closing each of their upper openings.

* * * * *

UNITED STATES PATENT AND TRADEMARK OFFICE
CERTIFICATE OF CORRECTION

PATENT NO. : 7,909,191 B2  Page 1 of 1
APPLICATION NO. : 11/446613
DATED : March 22, 2011
INVENTOR(S) : Baker et al.

It is certified that error appears in the above-identified patent and that said Letters Patent is hereby corrected as shown below:

Column 1 delete the paragraph spanning lines 7-13:

"The present application is a regular, continuation-in-part patent application of U.S. Provisional Patent Application Ser. No. 60/687,510, filed June 3, 2005, entitled "Connectable Instrument Trays for Creating a Modular Case" which is hereby incorporated by reference in its entirety. The present application claims the benefit of U.S. Provisional Patent Application Ser. No. 60/687,510."

Column 1 line 7 insert the following paragraph:

-- This application claims the benefit of U.S. Provisional Patent Application Ser. No. 60/687,510, filed June 3, 2005, entitled "Connectable Instrument Trays for Creating a Modular Case" which is hereby incorporated by reference in its entirety. --

Signed and Sealed this
Eleventh Day of September, 2012

David J. Kappos
*Director of the United States Patent and Trademark Office*